US011934594B2

(12) United States Patent
Diolaiti et al.

(10) Patent No.: US 11,934,594 B2
(45) Date of Patent: Mar. 19, 2024

(54) SYSTEMS AND METHODS OF DEVICE CONTROL WITH OPERATOR AND MOTION SENSING

(71) Applicant: Intuitive Surgical Operations, Inc., Sunnyvale, CA (US)

(72) Inventors: Nicola Diolaiti, Menlo Park, CA (US); Benjamin L. Lee, Santa Clara, CA (US); Shu-Wen Yu, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 241 days.

(21) Appl. No.: 17/278,120

(22) PCT Filed: Sep. 26, 2019

(86) PCT No.: PCT/US2019/053186
§ 371 (c)(1),
(2) Date: Mar. 19, 2021

(87) PCT Pub. No.: WO2020/072272
PCT Pub. Date: Apr. 9, 2020

(65) Prior Publication Data
US 2021/0349559 A1 Nov. 11, 2021

Related U.S. Application Data

(60) Provisional application No. 62/741,222, filed on Oct. 4, 2018.

(51) Int. Cl.
G06F 3/0354 (2013.01)
G05B 15/02 (2006.01)
(52) U.S. Cl.
CPC ......... G06F 3/03549 (2013.01); G05B 15/02 (2013.01)

(58) Field of Classification Search
CPC ...... G06F 3/0213; G06F 3/0312; G06F 3/033; G06F 3/0354; G06F 3/03549;
(Continued)

(56) References Cited

U.S. PATENT DOCUMENTS

2002/0167482 A1* 11/2002 Yin ................. G06F 1/1616
345/156
2004/0196260 A1* 10/2004 Lin ................. A63F 13/24
345/161
(Continued)

FOREIGN PATENT DOCUMENTS

EP 2480158 A1 8/2012
WO WO-2018112216 A1 6/2018
WO WO-2018165047 A1 9/2018

OTHER PUBLICATIONS

International Search Report and Written Opinion for Application No. PCT/US2019/053186, dated Feb. 20, 2020, 14 pages.
(Continued)

Primary Examiner — Priyank J Shah
(74) Attorney, Agent, or Firm — Haynes & Boone, LLP

(57) ABSTRACT

Systems and methods for operation of a medical device may include at least two sensors to confirm a command to control a medical instrument is intentionally made by an operator. The systems may include an operator-detection sensor associated with an input device and configured to detect a presence of an operator at the input device. The systems may also include a motion sensor associated with the input device and configured to detect a displacement distance of the input device. A control unit may use a displacement threshold for the input device and may be configured to permit or prevent control signal generation based on feedback from the at least two sensors.

19 Claims, 12 Drawing Sheets

(58) Field of Classification Search
CPC ........ B25J 9/1689; A61B 34/25; A61B 34/30; A61B 34/35; A61B 34/74–77
See application file for complete search history.

(56) References Cited

U.S. PATENT DOCUMENTS

| | | |
|---|---|---|
| 2011/0238010 A1* | 9/2011 | Kirschenman .... A61M 25/0105 604/95.04 |
| 2014/0108992 A1 | 4/2014 | Bi et al. |
| 2015/0031953 A1* | 1/2015 | Atarot ................ A61B 1/00042 600/118 |
| 2016/0095072 A1 | 3/2016 | Lee et al. |
| 2018/0349583 A1* | 12/2018 | Turgeman ........... H04L 63/0861 |
| 2019/0294265 A1* | 9/2019 | Lee ....................... G06F 3/0362 |
| 2020/0142488 A1* | 5/2020 | Unnikrishnan ..... G06F 3/03543 |
| 2020/0179068 A1* | 6/2020 | Peine .................... A61B 34/35 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/053186, dated Apr. 15, 2021, 08 pages.

\* cited by examiner

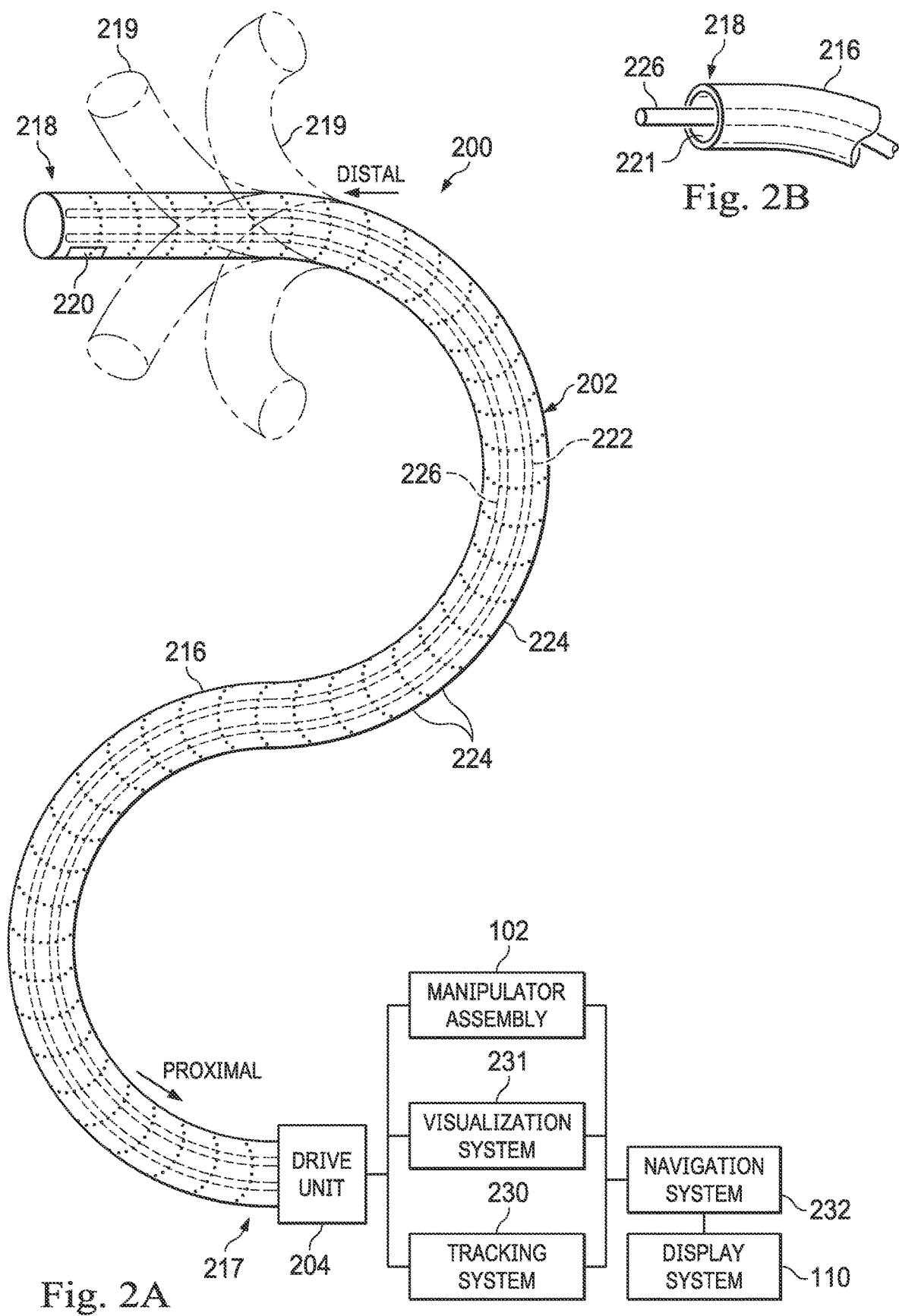

SYSTEMS AND METHODS OF DEVICE CONTROL WITH OPERATOR AND MOTION SENSING

CROSS-REFERENCE TO RELATED APPLICATIONS

This application is a Section 371 United States national phase application of PCT application PCT/US2019/053186, filed Sep. 26, 2019, which claims the benefit of U.S. Provisional Application 62/741,222 filed Oct. 4, 2018, which is related to PCT Patent Application PCT/US2018/044419 (ISRG10760/PCT; 70228.619WO01) all of which are incorporated by reference herein in their entireties.

FIELD

Examples described herein relate to systems and methods for safely operating a device, such as a steerable elongate medical device, using an input control console.

BACKGROUND

Minimally invasive medical techniques may be intended to reduce the amount of tissue that is damaged during medical procedures, thereby reducing patient recovery time, discomfort, and/or harmful side effects. Such minimally invasive techniques may be performed through natural orifices in a patient anatomy or through one or more surgical incisions. Through these natural orifices or incisions, clinicians may insert minimally invasive medical instruments (including surgical, diagnostic, therapeutic, and/or biopsy instruments) to reach a target tissue location. A minimally invasive technique may use a flexible and/or steerable elongate device, such as a catheter, that can be inserted into anatomic passageways and navigated toward a region of interest within the patient anatomy. Control of the elongate device by medical personnel can involve the management of several degrees of freedom including at least the management of insertion and retraction of the elongate device as well as steering of the device in a teleoperated manner using a master assembly. In addition, different modes of operation may also be supported.

Operation of a medical device, such as a flexible and/or steerable elongate device within the body of a patient, using a master assembly may present risks to the patient when the master assembly is inadvertently or accidentally actuated.

Accordingly, it would be advantageous to provide systems and methods that help limit undesirable damage to subject materials, such as the tissue of a patient, when commanding motion of a device.

SUMMARY

The following presents a simplified summary of various examples described herein and is not intended to identify key or critical elements or to delineate the scope of the claims.

Consistent with some embodiments, a control system for a device includes a memory and a processor coupled to the memory. The processor may be configured to determine, using one or more sensors, operator contact with a first input control of an input control console coupled to the system.

In some example aspects, the present disclosure is directed to a system that may include an input device configured to be utilized by an operator to control a medical device, an operator-detection sensor associated with the input device and that may be configured to detect a presence of an operator at the input device, and a motion sensor associated with the input device and that may be configured to detect a displacement distance of the input device. A control unit may permit or prevent control signal generation based on whether the detected displacement distance exceeds a displacement threshold for the input device while detecting that an operator is present at the input device.

In some aspects, the operator-detection sensor may comprise a capacitive sensor configured to detect when the operator is in physical contact with the input device. In some aspects, the control unit may comprise the displacement threshold for the input device stored therein. In some aspects, the control unit may be configured to prevent control signal generation when the detected displacement distance exceeds the displacement threshold while the operator-detection sensor detects that the operator is present at the input device. In some aspects, the control unit may comprise a velocity cap stored therein. The control unit may be configured to compare a motion detected by the motion sensor to the displacement threshold and limit movement of the medical device to a velocity at or below the velocity cap. In some aspects, the control unit may reset an accumulated travel distance of the input device when an operator present signal is not detected. In some aspects, the input device may comprise one or more of a rollable scroll wheel or a rollable trackball. In some aspects, the motion sensor may comprise an encoder configured to detect the displacement distance of the input device. In some aspects, the displacement threshold is less than or equal to an exposed surface distance of the input device. In some aspects, the control unit may store a plurality of displacement thresholds including the displacement threshold. The control unit select the displacement threshold of the plurality of displacement thresholds based on a context of a medical procedure to be performed. In some aspects, the context of the medical procedure to be performed may take into account at least one of: a type of surgery to be performed, a surgical site to be treated, a presence of a vision probe, a location of the medical device relative to sensitive tissue in a patient body, or a detected force resistance against the medical device. In some aspects, the control unit may comprise a displacement limit stored therein. The displacement limit may prevent generation of control signals that would move the medical device a displacement distance greater than the displacement limit when the medical device is disposed within a patient. In some aspects, the displacement limit may prevent generation of control signals when a request for displacement of the medical device greater than 4 mm is input at the input device and when the medical device is disposed within a patient. In some aspects, the displacement limit may prevent generation of control signals when a request for displacement of the medical device greater than 2 mm is input at the input device and when the medical device is disposed within a patient. In some aspects, the control unit may permit generation of control signals to displace the medical device in response to an input at the input device during a time period that the operator-detection sensor detects that the operator is present at the input device. In some aspects, the control unit may permit generation of the control signals after determining that the input at the input device is a command to displace the medical device. The command may be for a displacement less than the displacement threshold. In some aspects, the system may comprise an output device, the operator-detection sensor may comprise a capacitive sensor configured to detect presence of an operator based on a capacitance level exceeding a command capacitance level, and the control unit may be configured to instruct the output device to output a message to the operator to not touch the input device during calibration of the command capacitance level. In some aspects, the output device may comprise a display device. The message may comprise a visual message, and the control unit may instruct the display device to display the visual message during calibration of the command capacitance level. In some aspects, the operator-detection sensor may comprise a capacitive sensor configured to detect presence of an operator based on a capacitance level exceeding a command capacitance level. The control unit may be configured to: during calibration of the command capacitance level, detect, via the motion sensor, voluntary motion of the input device by the operator; and based on detection of the voluntary motion of the input device, initiate a recalibration of the command capacitance level. In some aspects, the system may comprise a display device, and the control unit may be configured to: based on the detection of the voluntary motion of the input device, instruct the display device to display a message to the operator to not touch the input device. In some aspects, the control unit may initiate the recalibration based on a determination that the voluntary motion of the input device is below a threshold motion of the input device. In some aspects, the determination that the voluntary motion of the input device is below the threshold motion may comprise a determination that a velocity of the voluntary motion is below a threshold velocity. In some aspects, the determination that the voluntary motion of the input device is below the threshold motion may comprise a determination that a duration of the voluntary motion is below a threshold duration. In some aspects, the control unit may initiate the recalibration based on detected motion of the input device over a length of time between than 0.5 and 5 seconds. In some aspects, the control unit may initiate calibration of a command line level for the operator-detection sensor based on: detecting, via the motion sensor, a voluntary motion by the operator, and detecting, via the operator-detection sensor, that the operator is not present at the input device.

In some example aspects, the present disclosure is directed to a method that may include detecting a presence of an operator at an input device configured to be utilized by an operator to control a medical device. The method may also include detecting, via a motion sensor, a displacement distance of the input device, and permitting or preventing generation of a control signal to displace the medical device based on whether the detected displacement distance exceeds a prestored displacement threshold while detecting the presence of the operator.

In some aspects, detecting the presence of the operator may comprise detecting that the operator is in contact with the input device by measuring a capacitance of the input device with a capacitance sensor. In some aspects, permitting or preventing generation of the control signal may comprise preventing generation of the control signal when the detected displacement distance exceeds the prestored displacement threshold while detecting the presence of the operator. In some aspects, the method may comprise comparing motion detected by the motion sensor to the prestored displacement threshold and limiting movement of the medical device to a velocity at or below a velocity cap based on the detected motion. In some aspects, detecting the displacement distance may comprise detecting the displacement distance on a surface of a rollable input device. In some aspects, the method may comprise selecting the prestored displacement threshold from a plurality of displacement thresholds based upon a context of a medical procedure to be performed.

In yet additional example aspects, the present disclosure is directed to a system that may comprise an input device configured to be utilized by an operator to control a medical device, an operator-detection sensor associated with the input device and configured to detect a presence of an operator at the input device, and a motion sensor associated with the input device and configured to detect a displacement distance of the input device. A control unit may, based on the detected displacement distance of the input device being below a displacement threshold and the detected presence of an operator, activate a velocity cap at a first velocity. The control unit also may, based on the detected displacement distance of the input device being above the displacement threshold and the detected presence of an operator, modify the velocity cap to a second velocity higher than the first velocity.

In some aspects, the operator-detection sensor may comprise a capacitance sensor configured to detect physical contact of the operator with the input device. In some aspects, the displacement threshold may be stored in the control unit. In some aspects, the motion sensor may comprise an encoder. In some aspects, the control unit may, when the operator-detection sensor detects the absence of the operator, prevent command signals to displace the medical device from being sent.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2A is a simplified diagram of a medical instrument system according to some embodiments.

FIG. 2B is a simplified diagram of a medical instrument with an extended medical tool according to some embodiments.

Figure 1:
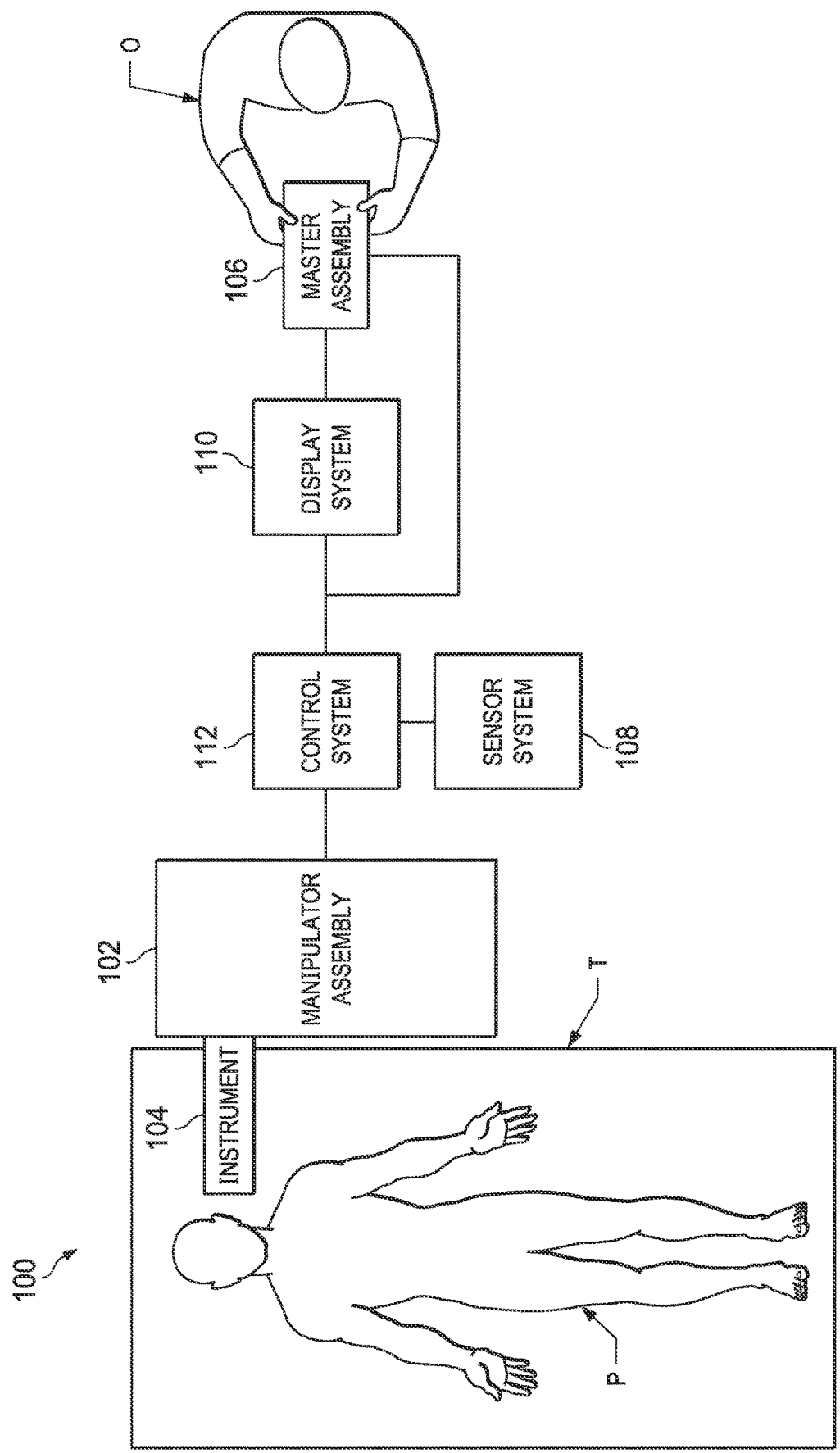
FIG. 1 is a simplified diagram of a medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances, well known methods, procedures, components, and circuits have not been described in detail so as not to unnecessarily obscure aspects of the embodiments.

This disclosure describes various instruments and portions of instruments in terms of their state in three-dimensional space. For example, the term position refers to the location of an object or a portion of an object in a three-dimensional space (e.g., three degrees of translational freedom along Cartesian x-, y-, and z-coordinates). The term orientation refers to the rotational placement of an object or a portion of an object (e.g., one or more degrees of rotational freedom, such as roll, pitch, and yaw). The term pose refers to the position of an object or a portion of an object in at least one degree of translational freedom and to the orientation of that object or portion of the object in at least one degree of rotational freedom (e.g., up to six total degrees of freedom). The term shape refers to a set of poses, positions, or orientations measured along an object.

FIG. 1 is a simplified diagram of a medical system 100 (e.g., a robotic medical system) according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used in robotic systems for animals, human cadavers, animal cadavers, portions of human or animal anatomy, non-surgical diagnosis, as well as for industrial systems and/or other general robotic systems.

As shown in FIG. 1, medical system 100 may include a manipulator assembly 102 for operating a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 may be mounted to and/or positioned near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is may be located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, scroll wheels, directional pads, buttons, data gloves, trigger-guns, hand-operated controllers, voice recognition devices, body motion or presence sensors, and/or the like.

Manipulator assembly 102 supports medical instrument 104 and may include a kinematic structure of one or more non-servo controlled links (e.g., one or more links that may be manually positioned and locked in place, generally referred to as a set-up structure), one or more servo controlled links (e.g., one or more links that may be controlled in response to commands from the control system), and/or a manipulator. Manipulator assembly 102 may include a plurality of actuators or motors that drive inputs on medical instrument 104 in response to commands from the control system (e.g., a control system 112). The actuators may include drive systems that when coupled to medical instrument 104 may advance medical instrument 104 into a naturally or surgically created anatomic orifice. Other drive systems may move the distal portion of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Medical system 100 may include a sensor system 108 with one or more sub-systems for receiving information about the manipulator assembly 102 and/or the medical instrument 104. Such sub-systems may include a position/location sensor system (e.g., an electromagnetic (EM) sensor system); a shape sensor system for determining the position, orientation, speed, velocity, pose, and/or shape of a distal portion and/or of one or more segments along a flexible body that may make up medical instrument 104; a visualization system for capturing images from the distal portion of medical instrument 104; and/or actuator position sensors such as resolvers, encoders, potentiometers, and the like that describe the rotation and orientation of the motors controlling the instrument 104.

Medical system 100 may include a display system 110 for displaying an image or representation of the surgical site and medical instrument 104. In some examples, display system 110 may present pre-operative or intra-operative images of a surgical site using image modalities such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In some embodiments, medical instrument 104 may include a visualization system that includes an image capture assembly to record a concurrent or real-time image of a surgical site and to provide the image to the operator O through one or more displays of display system 110.

In some examples, medical system 100 may configure the displayed representations, the medical instrument 104, and the controls of master assembly 106 such that the relative positions of the medical instruments are similar to the relative positions of the eyes and/or hands of operator O. In this manner, operator O can manipulate medical instrument 104 and hand controls as if viewing the workspace in substantially true presence.

In some examples, such as for purposes of image-guided medical procedures, display system 110 may display a virtual navigational image in which the actual location of medical instrument 104 is registered (e.g., dynamically referenced) with the preoperative or concurrent images/model. This may be done to present the operator O with a virtual image of the internal surgical site from a viewpoint of medical instrument 104.

Medical system 100 may also include control system 112. Control system 112 includes at least one memory and at least one computer processor (not shown) for effecting control between manipulator assembly 102, medical instrument 104, master assembly 106, sensor system 108, and/or display system 110. Control system 112 also includes programmed instructions (e.g., a non-transitory machine-readable medium storing the instructions) to implement some or all the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions corresponding to processes disclosed herein and described in more detail below. In some implementations, control system 112 may support wireless communication protocols such as Bluetooth, Infrared Data Association protocols (IrDA), home radio frequency (HomeRF), the Institute of Electrical and Electronic Engineers (IEEE) 802.11, Digital Enhanced Cordless Telecommunications (DECT), and Wireless Telemetry.

In some examples, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104.

Control system 112 may obtain sensor data from sensor system 108 that is used to compute an approximate location of medical instrument 104 with respect to the anatomy of patient P. The system may implement the sensor system 108 to register and display the medical instrument together with preoperatively or intraoperatively recorded medical images. For example, PCT Publication WO 2016/191298 (published Dec. 1, 2016 and titled "Systems and Methods of Registration for Image Guided Surgery"), which is incorporated by reference herein in its entirety, discloses example systems.

Medical system 100 may further include operations and support systems such as illumination systems, articulation (e.g., steering) control systems, irrigation systems, and/or suction systems (not shown). In some embodiments, medical system 100 may include more than one manipulator assembly and/or more than one master assembly. The exact number of manipulator assemblies may depend on the medical procedure and space constraints within the operating room, among other factors. Master assembly 106 may be co-located or they may be positioned in separate locations. Multiple master assemblies may allow more than one operator to control one or more manipulator assemblies in various combinations.

FIG. 2A is a simplified diagram of a medical instrument system 200 according to some embodiments. Medical instrument system 200 includes elongate device 202, such as a flexible catheter, coupled to a drive unit 204. Elongate device 202 may include a flexible body 216 having proximal end 217 and tip portion or distal end 218.

FIG. 2B is a simplified diagram of flexible body 216 with medical instrument 226 extended according to some embodiments. Flexible body 216 may include a channel 221 sized and shaped to receive the medical instrument 226. In some embodiments, medical instrument 226 may be used for procedures such as diagnostics, surgery, biopsy, ablation, illumination, irrigation, suction, etc. Medical instrument 226 can be deployed through channel 221 of flexible body 216 and used at a target location within the anatomy. Medical instrument 226 may be, for example, an image capture probe, a biopsy instrument, a laser ablation fiber, and/or another surgical, diagnostic, or therapeutic tool. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 may be a biopsy instrument used to remove sample tissue or a sampling of cells from a target anatomic location. Medical instrument 226 may be advanced from the opening of channel 221 to perform the procedure and then retracted back into the channel 221 when the procedure is complete. Medical instrument 226 may be removed from proximal end 217 of flexible body 216 or from another optional instrument port (not shown) along flexible body 216.

Medical instrument 226 may house cables, linkages, or other actuation controls (not shown) that extend between its proximal and distal ends to controllably bend distal end of medical instrument 226. Steerable instruments are described in detail in U.S. Pat. No. 7,316,681 (titled "Articulated Surgical Instrument for Performing Minimally Invasive Surgery with Enhanced Dexterity and Sensitivity") and U.S. Pat. No. 9,259,274 (titled "Passive Preload and Capstan Drive for Surgical Instruments"), which are incorporated by reference herein in their entireties.

Flexible body 216 may also or alternatively house cables, linkages, or other steering controls (not shown) that extend between drive unit 204 and distal portion 218 to controllably bend distal portion 218 as shown, for example, by broken dashed line depictions 219 of distal portion 218. In some examples, at least four cables are used to provide independent up-down steering to control a pitch of distal portion 218 and left-right steering to control a yaw of distal end 281. Steerable elongate devices are described in detail in U.S. Pat. No. 9,452,276 (titled "Catheter with Removable Vision Probe"), which is incorporated by reference herein in its entirety. In embodiments where medical instrument system 200 is actuated by a teleoperational assembly, drive unit 204 may include drive inputs that removably couple to and receive power from drive elements, such as actuators, of the teleoperational assembly. In some examples, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal portion 218. In some examples, one or more lumens, through which medical instruments can be deployed and used at a target anatomical location, may be defined by the walls of flexible body 216. In some examples, medical instrument system 200 may be teleoperated within medical system 100 of FIG. 1. In some examples, manipulator assembly 102 of FIG. 1 may be replaced by direct operator control.

Figure 3A:
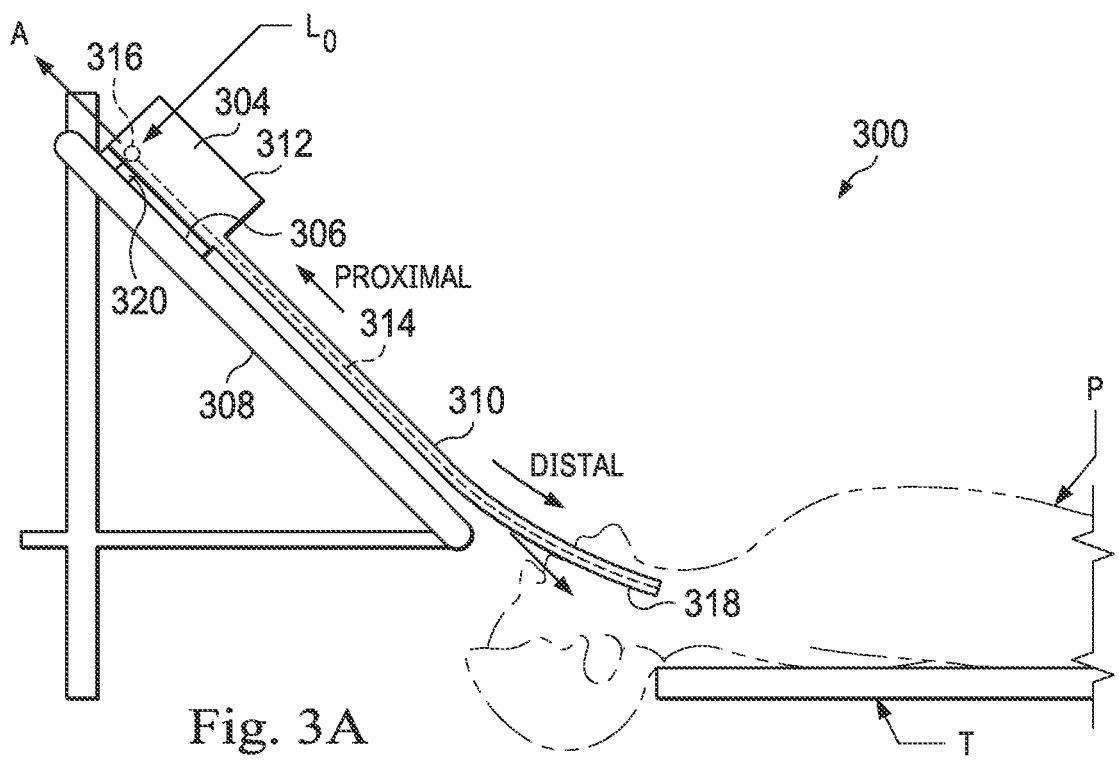
FIGS. 3A and 3B are simplified diagrams of side views of a patient coordinate space including a medical instrument mounted on an insertion assembly according to some embodiments.
Figure 3B:
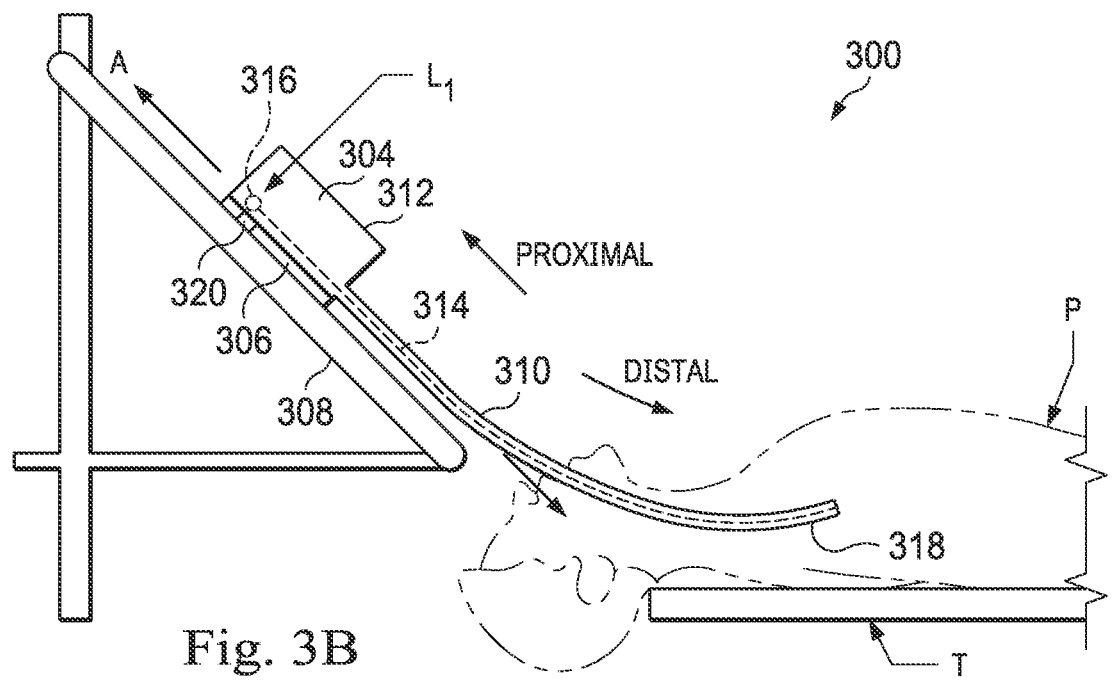

FIGS. 3A and 3B are simplified diagrams of side views of a patient coordinate space including a medical instrument mounted on an insertion assembly according to some embodiments. As shown in FIGS. 3A and 3B, a surgical environment 300 may include a patient P is positioned on platform 302. Instrument carriage 306 may be mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal portion 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308. Elongate device 310 is coupled to an instrument body 312. Instrument body 312 is coupled and fixed relative to instrument carriage 306. A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

Elongate device 310 may also include one or more sensors (e.g., components of the sensor system 108). In some examples, an articulation sensor 314, such as a fiber optic shape sensor, may be fixed on instrument body 312. Articulation sensor 314 may measure a shape from the proximal end to another location, such as a distal portion of the elongate device 310. Articulation sensor 314 may be aligned with the flexible elongate device 310 (e.g., provided within an interior channel (not shown) or mounted externally).

FIG. 3A shows instrument body 312 and instrument carriage 306 in a retracted position along insertion stage 308. With this retracted position of instrument body 312 and instrument carriage 306, distal portion 318 of elongate device 310 may be positioned just inside an entry orifice of patient P. In FIG. 3B, instrument body 312 and instrument carriage 306 have advanced along the linear track of insertion stage 308 and distal portion 318 of elongate device 310 has advanced into patient P.

Control of a flexible elongate device (e.g., elongate device 202 having flexible body 216, elongate device 310, and/or a flexible catheter) may involve simultaneous control of multiple degrees of freedom. In some examples, to control insertion and/or retraction of the elongate device and correspondingly an insertion depth of the distal portion of the elongate device, such as distal portion 218 and/or 318, one or more actuators, such as the one or more actuators controlling the position of instrument carriage 306 along insertion stage 308, are used. Commands to the one or more actuators may be received from operator O using a single degree of freedom input control, such as a lever, joystick, and/or the like. In some examples, to control the steering of the distal portion, the steering unit for the distal portion, such as drive unit 204, may be provided with both pitch and yaw instructions. The pitch and yaw instructions may be received from operator O using a two-degree of freedom input control, such as a joystick. Because control of the elongate device may include concurrently providing insertion and/or retraction instructions along with steering instructions, the input controls for insertion and/or retraction and steering may be separate from each other.

For certain procedures, the use of levers and/or joysticks as the input controls for the elongate devices of FIGS. 2A, 3A, and/or 3B can be less than ideal. This is because levers and joysticks are input controls that have a finite length of travel, which may be disproportionately short relative to the length of insertion travel and/or the range of steering necessary to access certain anatomy. Thus, use of the levers and/or joysticks as positional input devices that provide a limited insertion depth, pitch setting, and/or yaw setting can be inadequate. Input controls with a finite length of travel may be used as velocity input devices where movement of either input control specifies three velocity settings (reverse, idle, and forward) for switch-type input controls or variable velocity settings for proportional type input controls. However, velocity-based control of the insertion depth, pitch setting, and/or yaw setting may be unsatisfactory for high-precision manipulation of the elongate device because the control of the velocity of the distal end might not intuitively correspond with desires to make small high-precision changes in the insertion depth, pitch setting, and/or yaw setting, which is may be required for teleoperated minimally invasive medical procedures.

Alternatively, input controls offering an infinite length of travel can be used as input controls for the elongate device when accessing certain anatomy. Input controls with an infinite length of travel may correspond to input controls that allow continued movement of the inputs controls in a particular direction where no stop, such as a mechanical stop, restricts further movement. One example of a one degree of freedom input control with an infinite length of travel is a rollable scroll wheel, which may be spun unendingly in either direction. One example of a multiple-degree of freedom input control with an infinite length of travel is a trackball, which may be spun unendingly about any number of axes, which in practice may be decomposed into combinations of a left and right rotation, a forward and back rotation, and a spin in place rotation. Other examples of input controls that support an apparent infinite length of travel are input controls that support directional swipes without movement of the input control. Examples of directional swipe input controls are touch pads, touch screens, and/or the like.

Figure 4A:
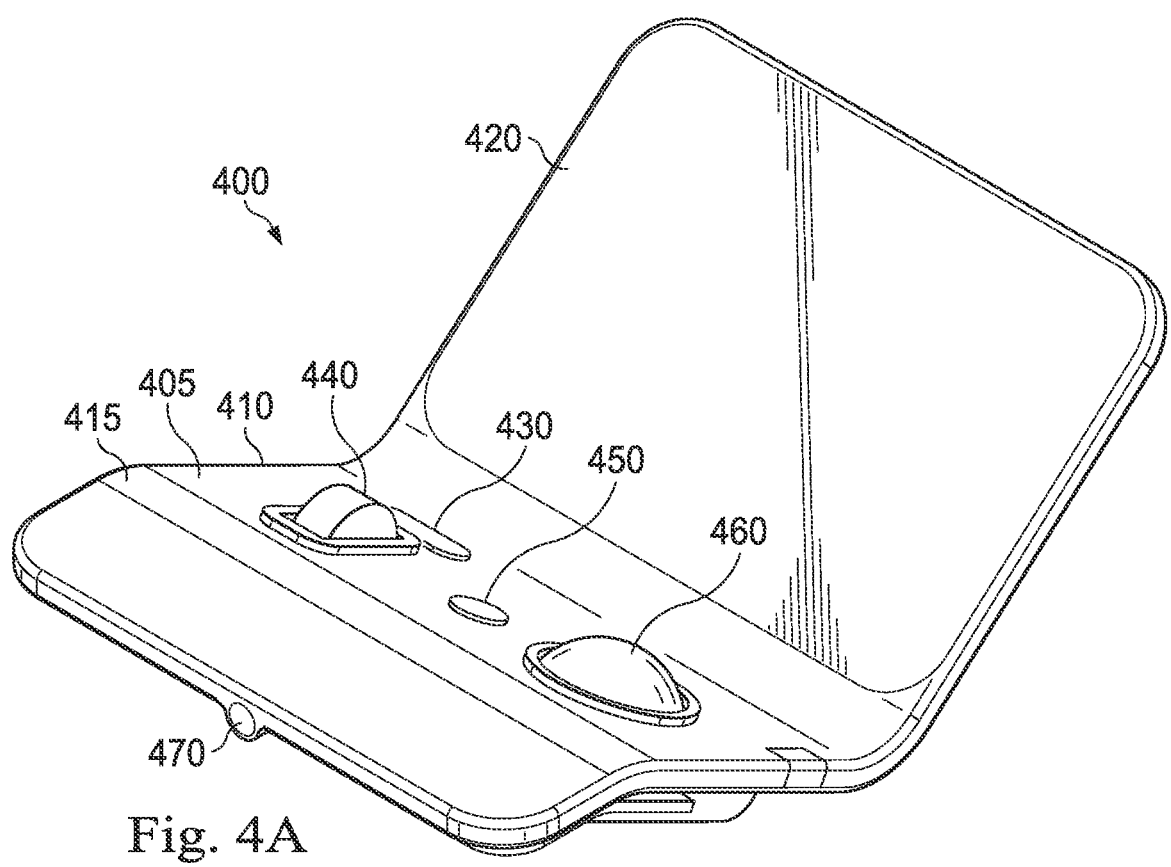
FIGS. 4A and 4B are simplified perspective diagrams of an input control console according to some embodiments.
Figure 4B:
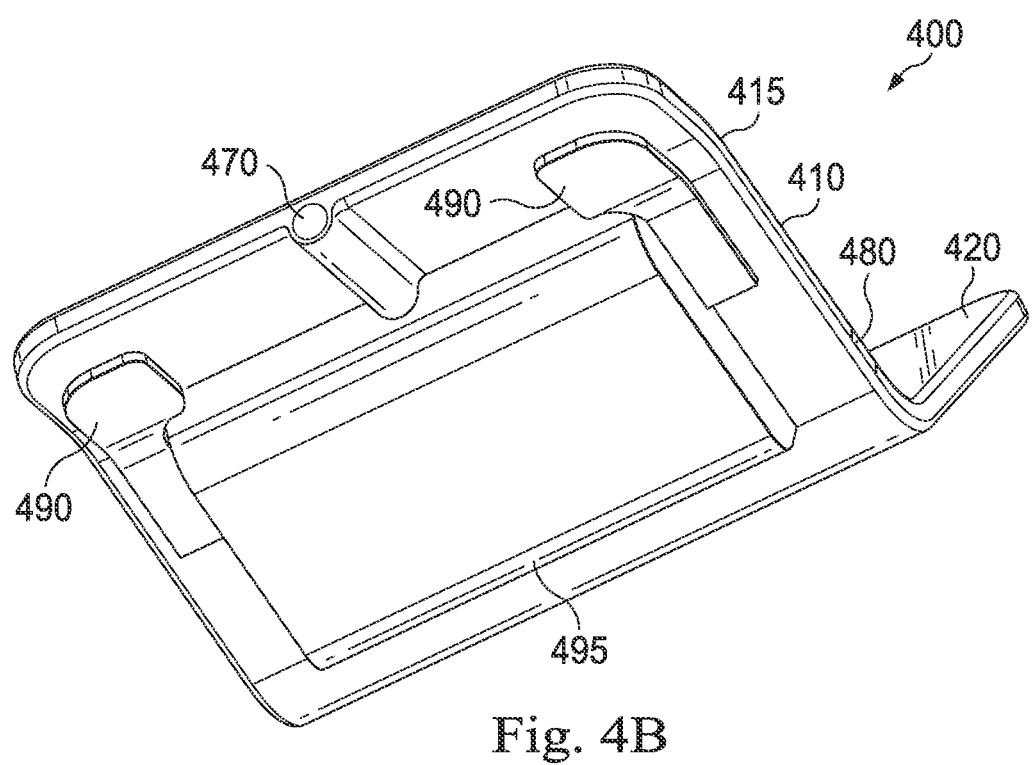

FIGS. 4A and 4B are simplified perspective diagrams of an input control console 400 according to some embodiments. FIG. 4A shows a top view of input control console 400, and FIG. 4B shows a bottom view of input control console 400. A top surface 405 of input control console 400 may include various input controls including a camera cleaning button 430, an insertion/retraction control 440, a passive control button 450, and a steering control 460. Although FIGS. 4A and 4B show configurations of the various input controls for an elongate device, it should be understood that input control console 400 can control any variety of instruments and devices and the exact placement, orientation, relative-positioning, and/or the like of the various input controls are illustrative only. It is understood that other configurations of input controls, different numbers of input controls, and/or the like are possible. In some embodiments, input control console 400 may be used as a patient-side input control unit for the elongate device and may, for example, be mounted in proximity to insertion stage 308.

Although not shown in FIGS. 4A and 4B, input control console 400 may optionally include one or more circuit boards, logic boards, and/or the like that may be used to provide power, signal conditioning, interface, and/or other circuitry for input control console 400. In some examples, the one or more circuit boards, logic boards, and/or the like are useable to interface with the input control console 400 and its various input controls to a control unit for the elongate device. In some examples, the control unit of the elongate device corresponds to the control device of master assembly 106, control system 112, and/or the like. In some examples, the one or more circuit boards, logic boards, and/or the like may include memory and one or more processors (e.g., multi-core processors, field programmable gate arrays (FPGAs), application specific integrated circuits (ASICs)), and/or the like. In some examples, the memory may include one or more types of machine-readable media. Some common forms of machine-readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

In some examples, insertion/retraction control 440 may be a single degree of freedom and infinite length of travel input control providing infinite length of travel along a first axis. The insertion/retraction control 440 may be used by the operator to control the insertion depth of the distal portion of the elongate device. Insertion/retraction control 440 is depicted as a scroll wheel, but other types of input controls, including non-infinite length of travel input controls, are possible. In some examples, scrolling of the scroll wheel forward away from the operator may increase the insertion depth (e.g., insertion) of the distal portion of the elongate device and scrolling of the scroll wheel backward toward the operator may decrease the insertion depth (e.g., retraction) of the distal portion of the elongate device. In some examples, insertion/retraction control 440 may be used by the operator to move instrument carriage 306 in and out along insertion stage 308 in order to control the insertion depth of distal portion 318.

When insertion/retraction control 440 is an infinite length of travel input control, operating insertion/retraction control 440 in a position-specifying mode may allow the operator to exercise precise insertion depth control of the distal portion of the elongate device over the full length of travel of the elongate device. In some examples, movement of insertion/retraction control 440 may be detected by the one or more circuit boards, logic boards, and/or the like of input control console 400 using one or more motion sensors such as encoders, resolvers, optical sensors, hall effect sensors, and/or the like (not shown). In some examples, feedback applied via one or more electromagnetic actuators, and/or the like may optionally be used to apply haptic feedback to insertion/retraction control 440. In some examples, an operator may adjust or customize a scale factor between an amount of movement of insertion/retraction control 440 and an amount of insertion and/or retraction movement by the elongate device. In some implementations, the scale factor adjustment may be made by control software of the elongate device. This adjustability may allow an insertion/retraction velocity of the elongate device to have either both fast insertion and retraction when desired and slower more precise insertion and retraction when greater control precision is desired. In some embodiments, insertion/retraction control 440 may optionally be touch sensitive (e.g., via capacitive touch detection) and/or have pressure sensitivity so that input control console 400 is able to differentiate between intended movement of insertion/retraction control 440 by the operator from inadvertent movement due to accidental contact, dropping of input control console 400, and/or the like.

In some examples, steering control 460 may be a multi-degree of freedom infinite length of travel input control providing infinite length of travel about any number of axes, which in practice may be decomposed into combinations of a left and right rotation, a forward and back rotation, and a spin in place rotation. Steering control 460 is depicted as a trackball, but other types of input controls, including non-infinite length of travel input controls, are possible. Steering control 460 may be used by the operator to concurrently control both the pitch and yaw of the distal end of the elongate device. In some examples, components of the trackball rotation in the forward and back directions may be used to control a pitch of the distal end of the elongate device and components of the trackball rotation in the left and right directions may be used to control a yaw of the distal end of the elongate device. In some examples, other rotational components of the trackball may be used to control pitch and/or yaw with the operator being optionally able to control whether the direction of rotation is normal and/or inverted relative to the direction applied to the steering (e.g., rotate forward to pitch down and backward to pitch up versus backward to pitch down and forward to pitch up). In some examples, steering control 460 may be used by the operator to manipulate the distances each of the cables extending between the proximal and distal portions of the elongate device are pushed and/or pulled.

When steering control 460 is an infinite length of travel input control, operating steering control 460 in a position-specifying mode may allow the operator to exercise precise steering of the distal end of the elongate device in both pitch and yaw concurrently so as to achieve precise control over an orientation of the distal end. In some examples, movement of steering control 460 may be detected by one or more circuit boards, logic boards, and/or the like of input control console 400 using one or more motion sensors such as encoders, resolvers, optical sensors, hall effect sensors, and/or the like (not shown). In some examples, feedback applied to the one or more electromagnetic actuators and/or the like may optionally be used to apply haptic feedback to steering control 460. In some examples, a scale factor between an amount of movement of steering control 460 and an amount of pitch and/or yaw imparted to the distal end of the elongate device is adjustable by the operator and/or control software of the elongate device. In some embodiments, steering control 460 may optionally be touch sensitive (e.g., via capacitive touch detection) and/or have pressure sensitivity so that input control console 400 is able to differentiate between intended movement of steering control 460 by the operator from inadvertent movement due to accidental contact, dropping of input control console 400, and/or the like.

In some embodiments, input control console 400 may optionally support a lock mode of operation. In the lock mode of operation, when input control console 400 detects loss of affirmative contact by the operator with insertion/retraction control 440 and/or steering control 460 (e.g., via the capacitive touch or pressure sensitive features of insertion/retraction control 440 and/or steering control 460), a rigidity of the elongate device may increase and/or insertion and/or retraction may be prevented. In the lock mode, a position and/or orientation of the distal end of the elongate device may be maintained at the position and/or orientation detected before loss of affirmative contact was detected.

Input control console 400 is provided as a representative example of possible input control consoles for a computer-assisted medical device, such as the elongate device of FIGS. 1-3B. Additional variations and/or configurations of input control consoles may be found in International Patent Application No. PCT/US2017/039808, filed on Jun. 28, 2017 and entitled "Systems and Methods of Steerable Elongate Device," and U.S. patent application Ser. No. 16/049,640 filed on Jul. 30, 2018, entitled "Systems and Methods for Steerable Elongate Device," and published as US 2019/0029770, both of which are incorporated by reference herein in their entireties.

Figure 4C:
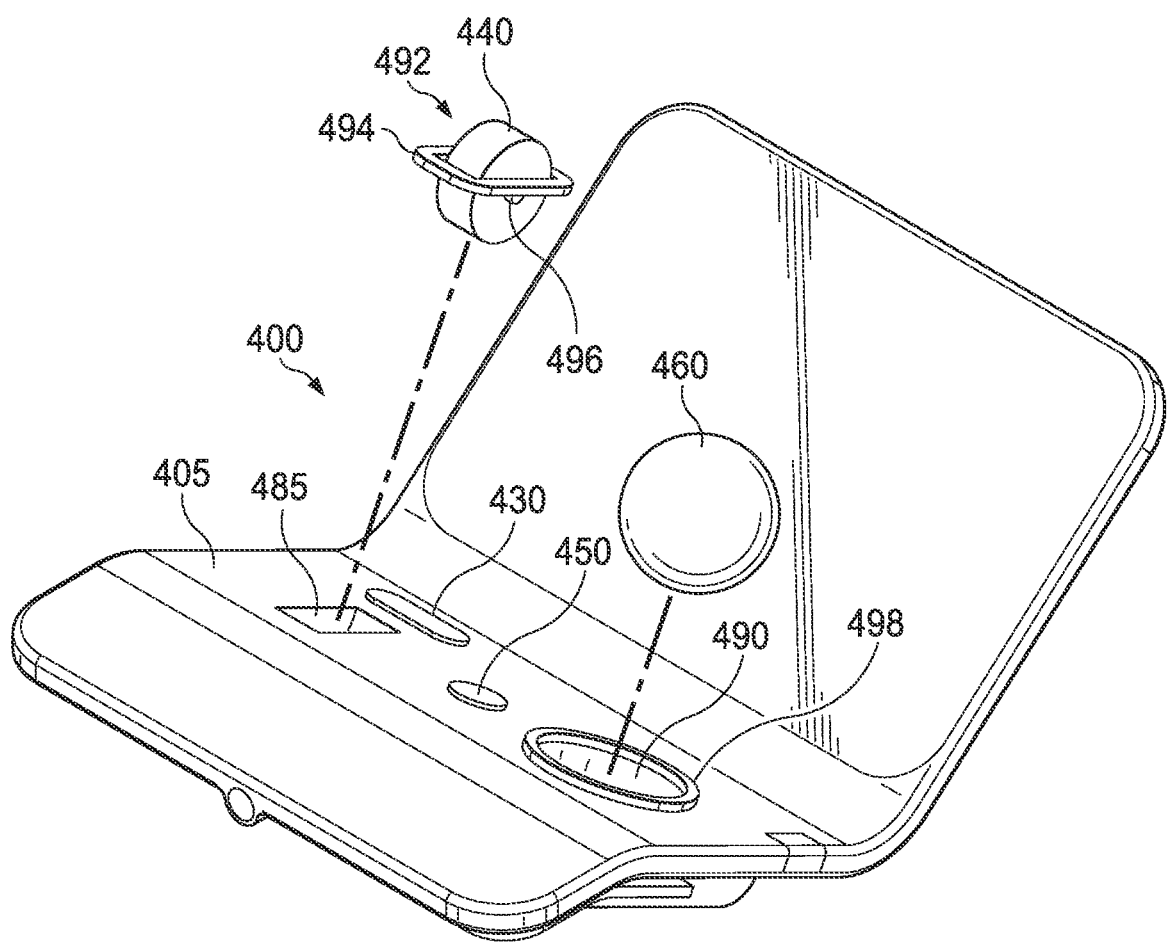
FIG. 4C is a simplified perspective diagrams of an input control console with removable input devices in a partially exploded configuration according to some embodiments.

FIG. 4C is a simplified perspective diagram of the input control console 400, such as in a cleaning condition, with some of the removable input controls removed according to some embodiments. In contrast, FIG. 4A shows the input control console 400 in an operating condition. The insertion/retraction control 440 and the steering control 460 may be removably disposed in the recesses 485 and 490, respectively as shown in FIG. 4C. Removal may further simplify cleaning and sterilization of the input controls, as well as the recesses 485 and 490.

In some embodiments, the complete input control console 400 may be a sealed unit. In some embodiments, the input control console 400 can be a liquid resistant unit where components, recesses, or breaks may be fully or partially sealed to liquid leakage. Accordingly, the input control console 400 may be protected from spilled liquids and can be sprayed and easily wiped for cleaning and sterilization. In some embodiments, the recesses 485 and 490 may be sealed with the top surface 405 of the input control console 400 so as to form a continuous, unbroken surface. The passive control button 450 and/or the camera cleaning button 430 may be sealed using conventional seals such as a silicon gasket. In some embodiments, the passive control button 450 and/or the camera cleaning button 430 may be formed of a touchpad or conductive button so to be flush with and a part of the top surface 405. This may further simplify cleaning of the top surface 405 of the input control console 400.

The insertion/retraction control 440 may be a part of a removable control assembly 492 that includes the insertion/retraction control 440 as a scroll wheel, a recess bracket 494, and an integrated axle 496. The recess bracket 494 may be sized to fit along the edge of the recess 485 and maintain the insertion/retraction control 440 in position for operation. The recess bracket 494 may also support the axle 496 about which the insertion/retraction control 440 rotates. The control assembly 492 may fit within the corresponding recess 485 and may be removed for cleaning or replacement.

A ring or lip 498 may extend around an edge of the recess 490. This may be sealed to and/or form a part of the surface 405 or may be removably attached to the surface 405. The removable steering control 460 may fit through the ring or lip 498 and into the recess 490. In some embodiments, half or more of the steering control 460 may protrude above the top surface 405. Although the ring or lip 498 and the recess bracket 494 are shown in FIG. 4C as protruding above the top surface 405, in some embodiments the ring or lip 498 and the recess bracket 494 may be flush with the top surface 405. In yet other embodiments, the ring or lip 498 and the recess bracket 494 may be recessed below the top surface 405. In the recess 490, the steering control 460 may float on one or more bearings and/or raised protrusions as will be described below, with reference to FIG. 5 for suspending the steering control 460. The bearing or raised protrusions may be roller bearings, point contact bearings, or other bearings or protrusions that provide support to the steering control 460 by rolling or providing non-rolling protrusion contacts, as described with reference to FIG. 5. A magnet fixture (not shown) may be provided to simplify removal of the steering control 460 from the recess 490. The magnet fixture may include magnets powerful enough to overcome the weight of the steering control 460 and other forces holding the steering control 460 in the recess 490. The magnet fixture may be used to lift the steering control 460 from the recess.

In some implementations, each recess 485 and 490 may include or be formed of an opaque cup. The opaque cup may be sealed and may include one or more transparent regions or windows. Some embodiments include an entirely transparent cup. The transparent regions or windows or the entirely transparent cup may be associated with one or more motion sensors, such as encoders, optical sensors, magnetic Hall effect sensors, or other types of sensors for sensing and tracking movement of the insertion/retraction control 440 and/or the steering control 460, as described herein. In some embodiments, the ring or lip 498 may be the upper edge of the opaque or transparent cup and may be flush with the top surface 405. In some embodiments, retention magnets may be disposed within or adjacent the recesses 485 and 490 to help retain the steering control 460 and/or the removable control assembly 492 therein. In some examples, the recesses 485 and 490 may be associated with one or more contact sensors for detecting affirmative contact by the operator with the steering control 460 and/or the insertion/retraction control 440. Some examples of the input control console 400 include one or more electromagnetic actuators and/or the like to apply haptic feedback to the steering control.

Figure 5:
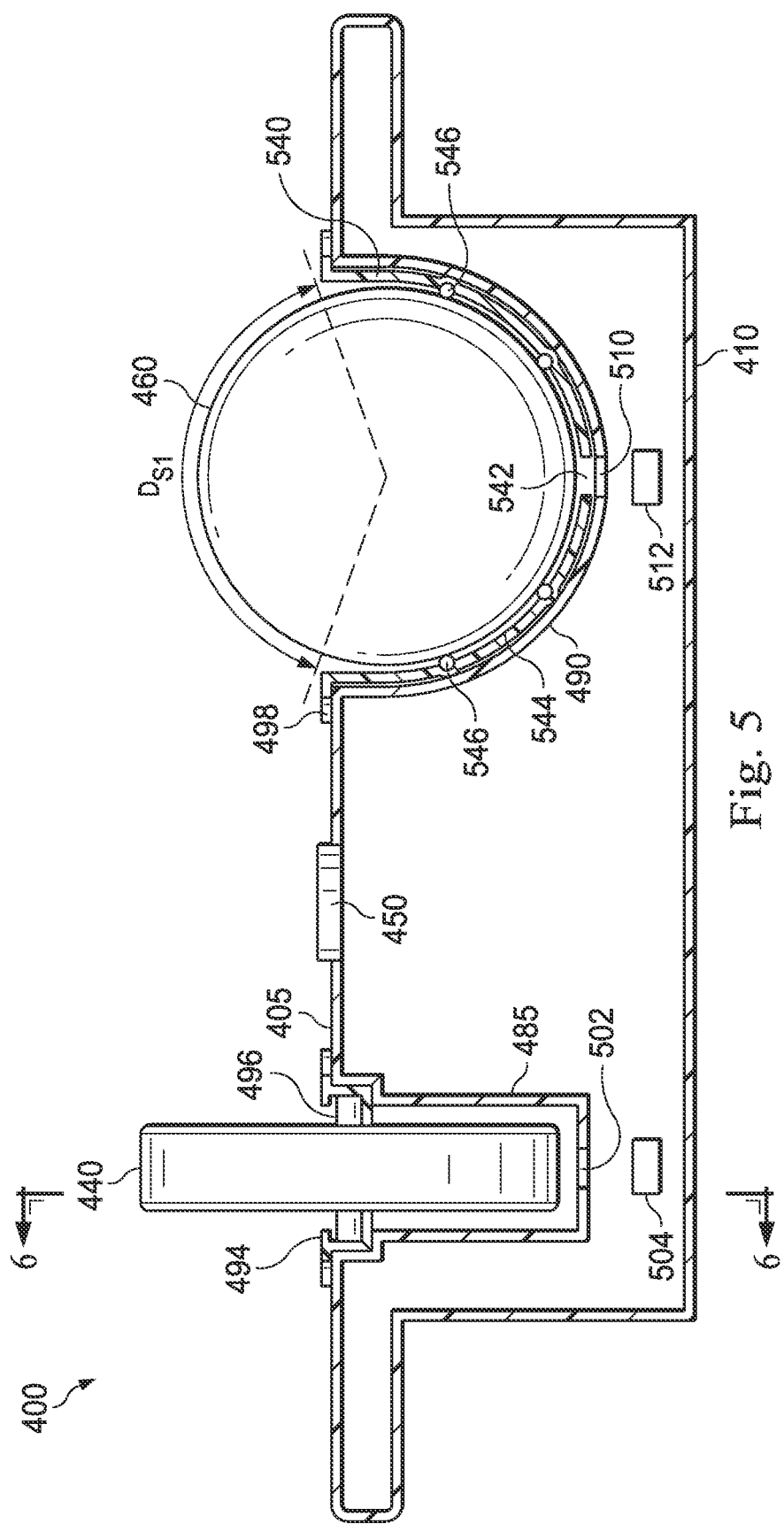
FIG. 5 is a simplified partial cross-sectional of an input control console according to some embodiments.

FIG. 5 is a simplified front partial cut-away view of the input control console 400 according to some embodiments. As shown in FIG. 5, the cut-away of a console body 410 is shown near a centerline of the insertion/retraction control 440 depicted as a scroll wheel, the passive control button 450, and the steering control 460 depicted as a trackball, although different alignments of the controls, different styles of the controls, and/or different placements of the controls are possible as would be understood in the art.

The console body 410 includes the recess 485, which may include one or more transparent windows 502 associated with one or more motion sensors 504, such as encoders, resolvers, optical sensors, hall effect sensors, and/or the like for sensing and tracking movement of an insertion/retraction control, such as insertion/retraction control 440. Although window 502 is shown at the bottom of recess 485, it may optionally be located at other locations within recess 485 to monitor the insertion/retraction control. In some examples, the one or more motion sensors may be non-optical (e.g., a magnetic hall effect sensor) and window 502 may be optional. For example, the motion sensor 504 may be disposed directly on the insertion/retraction control 440. In some implementations, the motion sensor 504 may be disposed on the axle 496 or otherwise disposed about the insertion/retraction control 440.

In some examples, recess 485 may be sufficiently deep so that less than half of the insertion/retraction control 440 extends above an upper surface of console body 410. Recess 485 may be sealed to support cleaning and/or sterilization of input control console 400. Recess 485 may additionally be associated with one or more contact sensors (not shown) for detecting affirmative contact by the operator with the insertion/retraction control. The one or more contact sensors may include one or more capacitive touch, pressure, and/or similar sensors. One or more electromagnetic actuators, and/or the like (not shown) may optionally be used to apply haptic feedback to the insertion/retraction control.

Input control console 400 may include the passive control button 450. In the example shown in FIG. 5, the passive control button 450 is shown protruding above the console body 410, but a flush-mounted or recessed button or other control is also possible.

Console body 410 may include the second recess 490. Recess 490 may include one or more transparent windows 510 associated with one or more motion sensors 512, such as encoders, resolvers, optical sensors, hall effect sensors, and/or the like for sensing and tracking movement of a steering control, such as steering control 460. Although window 510 is shown at the bottom of recess 490, it may optionally be located at other locations within recess 490 to monitor the steering control. In some examples, the one or more motion sensors 512 may be non-optical (e.g., a magnetic hall effect sensor) and window 510 may be optional. For example, the motion sensor 512 may be disposed directly on the steering control 460. In some implementations, the motion sensor 512 may be disposed on the interior surface of the second recess 490 or elsewhere about the steering control 460. In implementations where the motion sensor 512 is an encoder, the encoder may be disposed on the molding forming the ring or lip 498.

Recess 490 may be sufficiently deep so that less than half of the steering control 460 extends above an upper surface of console body 410 in the example shown. In some examples, recess 490 may include retention magnets (not shown) such that a corresponding steering control, such as steering control 460, can include magnetic or ferromagnetic material which aids in retaining the steering control within recess 490. Recess 490 may be sealed to support cleaning and/or sterilization of input control console 400. Recess 490 may additionally be associated with one or more contact sensors (not shown) for detecting affirmative contact by the operator with the steering control. The one or more contact sensors may include one or more capacitive touch, pressure, and/or similar sensors. One or more electromagnetic actuators, and/or the like (not shown) may optionally be used to apply haptic feedback to the steering control.

FIG. 5 further shows an integrated molding 540 for receiving the steering control 460 insertable in the recess 490 in the top of the input control console 400. The molding 540 may be configured to receive the moving parts of the steering control 460. Depending upon the embodiment, the moving part of the steering control may optionally include one or more retaining mechanisms to keep it seated within the molding 540. For example, the rollable trackball portion of the steering control 460 may be magnetically held within the molding 540 and the recess 490. The moving parts of the steering control 460 may be optionally retained using other mechanisms as well. The molding 540 may include one or more slots or openings 542 that are aligned with the one or more windows 510 in recess 490. Like the one or more windows 510, the one or more openings 542 may be located in positions other than the bottom of molding 540.

The molding 540 may further include the ring or lip 498 that extends beyond the edges of the recess 490. One or more retention magnets 544 may be located at intervals along the molding 540 to help position and align molding 540 relative to the recess 490. The one or more retention magnets 544 may be attracted to one or more corresponding magnets on the upper surface of console body 410 around the edges of recess 490.

Molding 540 may further include one or more bearings and/or raised protrusions 546 for suspending trackball steering control 460 above molding 540 and to allow less restricted rotational movement of the trackball steering control 460 relative to molding 540.

As can be seen in FIG. 5, the steering control 460 may include an exposed portion extending above the surface 405 of input control console 400. This exposed portion may generally define a maximum distance of rotation that the steering control may travel before a user is to reposition his or her hands to continue to steer the device. This maximum distance is labeled DS1 and represents the exposed surface distance of the trackball steering control 460.

Figure 6:
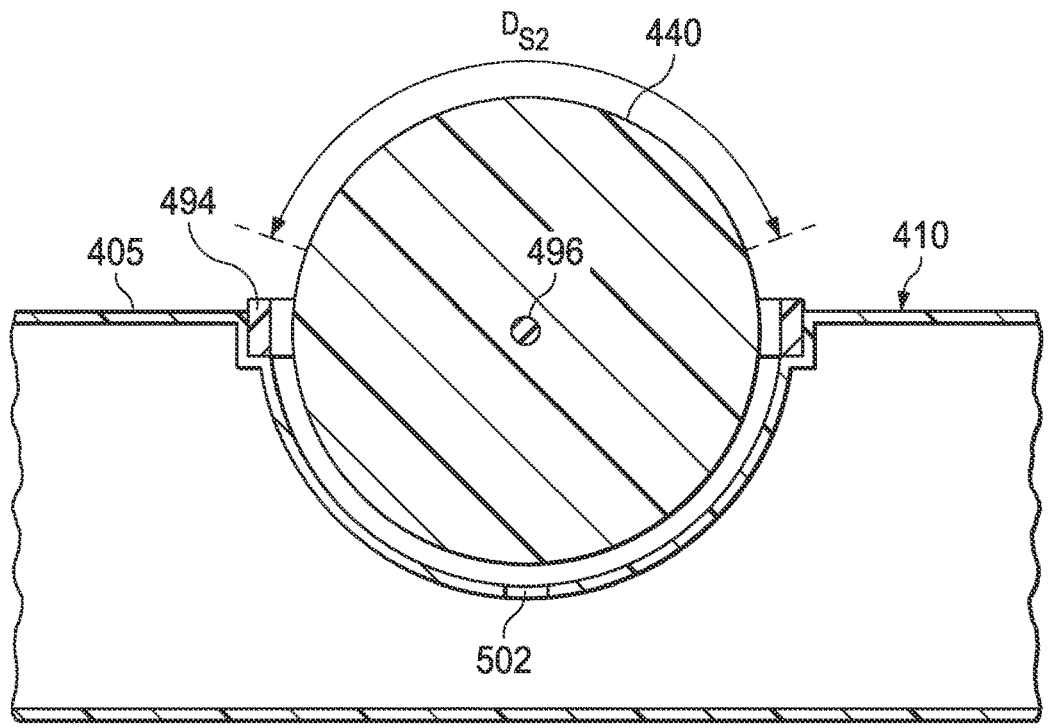
FIG. 6 is a simplified partial cross-sectional diagram of an input control console according to some embodiments.

FIG. 6 is a simplified cross-section of the input control console 400 taken along lines 6-6 in FIG. 5 through the insertion/retraction control 440. The insertion/retraction control 440 may include an exposed portion extending above the top surface 405 of the input control console 400. This exposed portion may generally define the maximum distance of rotation that the insertion/retraction control 440 may rotate before a user is to reposition his or her hands to continue to advance or retract the elongated device. This maximum distance is labeled DS2 and represents the exposed surface distance of the insertion/retraction control 440. The relevance of the maximum distances DS1 and DS2 will be explained further below.

Figure 7:
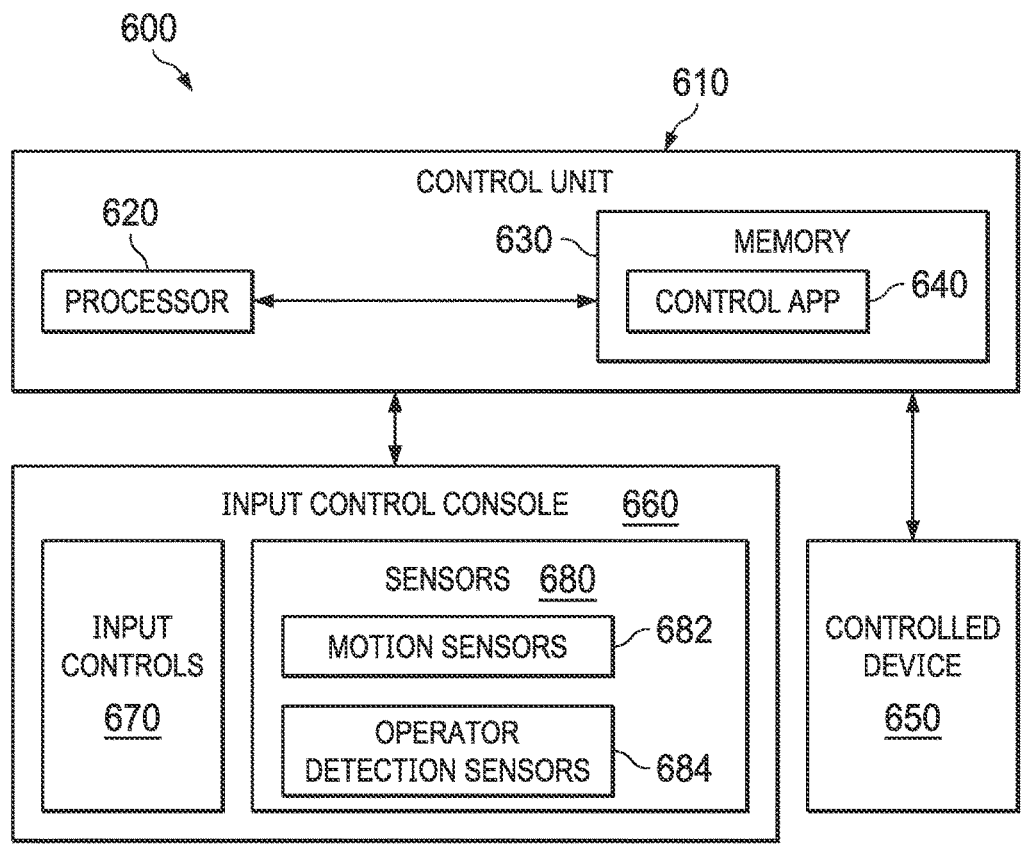
FIG. 7 is a simplified block diagram of a control system according to some embodiments.

FIG. 7 is a simplified diagram of a control system 600 according to some embodiments. The control system 600 may be configured to distinguish between an intentional input and an unintentional input at an input device, such as an insertion/retraction control 440 and/or the steering control 460 for controlling a medical instrument (e.g., the elongate device 202). Some examples of unintentional inputs at an input device may include inadvertent movement of the input device due to inadvertent contact, bumping the input device with a tool, a sleeve, or a portion of the operator's body, tipping of the control unit 610, or other inadvertent movement of the input device. The input device may include operator-detection sensors, such as capacitive sensors. Via the input controls, fluid spills or other materials may mimic the capacitive sensitivity of a human operator and may send false input signals from the input device.

The control system 600 described herein may operate in a manner to double check that an input at the input device was intentional and desired by an operator. It may do this by recognizing when inputs at an input device may have been unintentional. Accordingly, the control system 600 may be operable to reduce the likelihood of an inadvertent contact resulting in movement of a medical device inserted within and/or treating a patient. As described in some implementations herein, some inadvertent inputs may result in complete stoppage of a generated command signal. Other inadvertent inputs may result in command signal generation to move the medical tool, but may be maintained at a low velocity to give an operator time to stop or redirect the medical device to reduce a risk of introducing undesired trauma to a patient.

Some implementations described herein may utilize a multi (e.g., dual) detection system to more accurately predict when an input at the input device is intentional and should be performed (or unintentional and should be disregarded). To do this, the control system 600 may detect the presence of an operator at the input device and measure a distance traveled by the input device. For example, if a presence of an operator is undetected, or the input device is used to travel an unexpected distance, the control system may respond by taking steps to mitigate any undesired movement of the medical device. Using a dual-detection system to substantiate an input at an input device may increase the reliability and predictability of inputs at the input device.

In some embodiments, control system 600 may correspond to one or more portions of sensor system 108, display system 110, and/or control system 112 of FIG. 1. As shown in FIG. 7, control system 600 includes a control unit 610. Control unit 610 includes a processor 620 coupled to memory 630. Operation of control unit 610 may be controlled by processor 620. And although control unit 610 is shown with only one processor 620, it is understood that processor 620 may be one or more central processing units, multi-core processors, microprocessors, microcontrollers, digital signal processors, field programmable gate arrays (FPGAs), application specific integrated circuits (ASICs), and/or the like. Control unit 610 may optionally be implemented as a stand-alone subsystem and/or board added to a computing device or as a virtual machine. In some embodiments, control unit 610 may optionally be included as part of an operator workstation (not shown) and/or operated separately from, but in coordination with the operator workstation.

Memory 630 may be used to store software executed by control unit 610 and/or one or more data structures used during operation of control unit 610. Memory 630 may include one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 630 may include a control application 640 that supports autonomous, semiautonomous, and/or teleoperated control of a controlled device 650 coupled to control unit 610. In some examples, controlled device 650 may be a computer-assisted medical device, such as the elongate device of FIGS. 2A, 2B, 3A, and 3B. Control application 640 may include one or more control modules for controlling the drive units and/or actuators of controlled device 650 to control, for example, an insertion depth of controlled device 650, steer controlled device 650, operate an instrument at the distal end of controlled device 650, and/or the like. Control application 640 may also include one or more modules and/or application programming interfaces (APIs) for receiving position, motion, and/or other sensor information from controlled device 650. In some embodiments, one or more registration markers, fiducial markers, and/or the like mounted on controlled device 650 may be tracked using one or more tracking sensors, such as an imaging device, a shape sensor, and/or the like.

Control application 640 may further include one or more modules for interfacing with an input control console 660 being operated by an operator, such as operator O. In some examples, input control console 660 may be consistent with input control console 400. Control application 640 may receive control inputs from one or more input controls 670, which may include one or more of camera cleaning button 430, insertion/retraction control 440, passive control button 450, steering control 460, emergency stop button 470, and/or the like. Control application 640 may further include one or more modules for sending status information, images, haptic feedback, and/or the like to input control console 660. In some examples, the status information, images, and/or the like may be sent to input control console 660 for display on an integrated display screen, such as screen 420.

Control application 640 may further include one or more modules for interfacing with one or more sensors 680 of input control console 660. In some examples, the one or more sensors 680 may include one or more ways to detect whether commands from the one or more input controls 670, such as insertion, retraction, and/or steering commands, are being received via affirmative control by the operator using the one or more input controls 670 or from inadvertent movement of the one or more input controls 670, such as due to inadvertent contact, dropping of control unit 610, tipping over of control unit 610, and/or the like. The one or more sensors 680 may include, among other possible sensors, motion sensors 682 and operator-detection sensors 684. The motion sensor 682 may include the motion sensors 504 and 512 in FIG. 5 that monitor movement of the input devices, such as the insertion/retraction control 440 and the steering control 460. In some implementations, the motion sensors 682 may be, for example, encoders or other sensors. The operator-detection sensors 684 may be cooperatively associated with the input devices, such as the insertion/retraction control 440 and the steering control 460, in a manner that detects when an operator is present or affirmatively and intentionally contacting one or more of the input devices with his or her hand. The operator-detection sensors 684 may include, for example, affirmative contact capacitive touch sensors or other sensors. Although control application 640 is depicted as a software application, control application 640 may be implemented using hardware, software, and/or a combination of hardware and software.

The control application 640 may access and/or may include one or more displacement thresholds, velocity caps, and/or other thresholds and caps that may be relied upon to perform the control functions described herein. In some implementations, the thresholds are prestored thresholds within the control application 640. For example, the displacement thresholds may represent a limit relating to a distance that the input device may physically travel before the control application determines whether an input at the input device was intentional or unintentional. The displacement thresholds may be measurements of inches, centimeters or any unit, and may be specific to an input device, such as the insertion/retraction control 440 and/or the steering control 460. In some implementations, the displacement threshold may be based upon the exposed surface distance DS1 and DS2 labeled and identified in FIGS. 5 and 6. Depending on the embodiment, the displacement threshold may equal the exposed surface distances DS1 and DS2, or may be larger or smaller than the exposed surface distances. In some implementations, the prestored distance threshold may be in a range of about two full stroke distances of the scroll wheel or trackball. For example, the prestored distance threshold may correspond to about twice the exposed surface distance DS1 or DS2. In some implementations, the prestored distance threshold may be less than three full stroke distances (the exposed surface distances) of the input device, such as the scroll wheel or trackball. In some implementations, the prestored distance threshold may be in a range of about 1 to 2.5 full stroke distances of the scroll wheel or trackball. Since the insertion/retraction control 440 and the steering control 460 may have different diameters or may be placed at different depths in the input control console, the prestored distance threshold may be different for each.

In some implementations, the control application may use and/or include a plurality of displacement thresholds. During use, the control system 600 may operate using a first displacement threshold during a first scenario and a second different displacement threshold during a second scenario. In some implementations, these displacement thresholds may be dependent upon the context of the use of the medical instrument. For example, the displacement threshold may be dependent upon the type of surgery being performed, the surgical site to be treated, the presence of other instruments such as a vision probe, the location of the medical device relative to sensitive tissue in a patient body, and the detected force resistance against the medical device, as some non-limiting examples.

In some implementations of a control application with a plurality of displacement thresholds, the applied displacement threshold at any point in time may depend on the type of surgery being performed and/or the surgical site to be treated. For example, the displacement threshold used during a coronary artery bypass may be different than a displacement threshold used for gallbladder removal. Yet another displacement threshold may be utilized for taking a biopsy. The displacement threshold for each procedure may be based upon the sensitivity of the tissue, the size of the surgical site, and other factors that may be dependent upon the type of procedure being performed. Accordingly, the control application may access and/or store a plurality of different displacement thresholds, and the displacement threshold may be selected by an operator for use during a particular surgery. In some implementations, the different displacement thresholds may be selected using the integrated display screen 420, which may include selectable displacement thresholds or may include selectable surgical types.

In some implementations, the control application may use and/or include a plurality of thresholds that may depend on the presence of other instruments. For example, a first threshold may be used if a biopsy tool is being utilized, while a different second threshold may be utilized if an ablation is being performed. In other implementations, different thresholds may be used depending on the presence or absence of a vision probe or a type of vision probe.

In some implementations, the control application may include a plurality of thresholds that may depend on where the medical device is located relative to sensitive tissue in a patient body. The tip of the medical device may be tracked or calculated as it is introduced to the patient. When the tip of the medical device is passing through less sensitive tissue, the selected threshold may be greater than when the tip of the medical device is passing through more sensitive tissue.

In some implementations, the sensors 680 may include a force feedback measurement sensor. Based on the sensed feedback, the control application may select a displacement threshold from a plurality of displacement thresholds. When the force feedback sensor indicates that relatively higher forces are required to advance the instrument through a patient, then the selected displacement threshold may be low. However, when the force feedback sensor indicates that relatively lower forces are required to advance instrument through the patient, then the selected displacement threshold may be higher.

In some implementations, the control application 640 may also use and/or include a velocity profile defining one or more maximum velocity limits or caps. The velocity caps may be used to limit the speed of a response to an input at the input device. For example, a low velocity cap may be employed when the control system is less confident that an input at the input device was intentional, and a higher velocity cap may be employed when the control system is more confident that the input at the input device was intentional. The determination of whether to use a low velocity cap or a high velocity cap may depend on the detected state of the input device and the actual input at the input device.

Control unit 610 may be coupled to controlled device 650 and input control console 660 via an input/output (I/O) interface (not shown) that may include one or more drivers, signal conditioners, receivers, ports, and/or the like. The I/O interface may optionally include one or more cables, connectors, ports, and/or buses, and it may optionally further include one or more networks with one or more network switching and/or routing devices. In some examples, the I/O interface may optionally include wireless interfaces.

As indicated above, operation of controlled device 650 may raise some safety concerns regarding safety to controlled device 650 and/or a material, such as tissue of a patient, being manipulated by controlled device 650. In some examples, these safety concerns may be increased when controlled device 650 is controlled robotically and/or remotely, such as by using control unit 610 and input control console 660, and/or when one or more infinite length of travel input controls, such as the scroll wheel and/or trackball of an input control console, are used. In some examples, these safety concerns may be suitably mitigated by providing haptic feedback to the operator, displaying live images and/or tracking data to the operator (e.g., using screen 420), and/or the like. The use of these types of feedback, however, may be limited to cases where the operator is actively engaged with and using input control console 660, but may be of limited efficacy when the operations being commanded using input control console are due to inadvertent motion of the one or more input controls 670 (e.g., caused by accidental contact with the one or more input controls 670, dropping and/or tipping of input control console 660, and/or the like). Accordingly, improved safety in the operation of controlled device 650 may be obtained by using the one or more sensors 680 to differentiate between affirmative and desired control of the one or more input controls 670 by the operator and inadvertent control due to other causes.

Approaches to providing this improved safety are discussed in the context where controlled device 650 is an elongate device (e.g., the elongate device of FIGS. 1-3B) and input control console 660 is similar to input control console 400 and includes an insertion/retraction control (e.g., insertion/retraction control 440) and a steering control (e.g., steering control 460). However, it is understood that the improved safety features may be easily adaptable to other controlled devices and/or other input control consoles. Some controlled devices and/or input control consoles may include input controls similar to those described herein, while other controlled devices and/or other input control consoles may include or different input controls. The controlled devices and/or other input control consoles may control multiple devices in insertion/retraction, steering, roll, end effector actuation, and/or the like using either the same control console as disclosed herein with multiple input controls or using multiple control consoles with multiple input controls.

In some embodiments, controlling the motion of an elongate device may involve three types of motion: insertion motion where the distal end of the elongate device is advanced further into a material or passageway (a proximal to distal direction), retraction motion where the distal end of the elongate device is retreated along the path of the elongate device body (a distal to proximal direction), and steering motion where the distal end of the elongate device is bent in pitch or yaw. In some examples, the insertion and retraction may be controlled using a combined insertion/retraction control and the steering may be controlled by a separate steering control. In one example, detection of affirmative contact with the insertion/retraction control can allow for insertion/retraction control, while detection of affirmative contact with the steering control can allow for steering control. Of the three types of motion, the insertion motion may be subject to stricter safety procedures depending on a type of procedure to be performed and/or anatomy the procedure is performed within, but safety procedures may also be used for retraction or steering based on anatomy and/or procedure type. In some examples, these stricter safety procedures may include a) detecting the presence of the operator, including detecting affirmative contact and b) detecting an input displacement distance that is within an expected distance with both the insertion/retraction control and the steering control by the operator. Detecting both the presence of the operator and input displacement distance before allowing further insertion or advancement of the medical device into a patient body may prevent or reduce the chance of trauma introduced by inadvertent command at the input device. However, in some implementations, retraction of the medical device may be less protected because retraction typically might not have the same potential for trauma to a patient. Accordingly, retraction of the medical device may merely use detection of the presence of an operator, such as detecting affirmative contact with the insertion/retraction control before allowing retraction.

In some embodiments, controlling the motion of the elongate device may involve one or more additional types of motion. The one or more additional types of motion may include roll, rotation of a distal end of the elongate device, articulation of a distal end of the elongate device independent of the insertion and/or steering control, actuation of an end effector at the distal end of the elongate device, and/or the like. In some examples, the one or more additional types of motion may be controlled using one or more additional input controls. In some examples, the control console may include three or more input controls subject to the safety features described herein.

The motion sensors 682 may be used to confirm whether an operator is intentionally advancing, retracting, or steering an elongate device based on the assumption that an operator would need to lift his finger at some point during the motion after commanding a certain distance. Because the input devices have a limited distance of exposed surface, represented by DS1 and DS2 in FIGS. 5 and 6, the operator would be forced to lift his or her finger in order to drive the device from one stroke to another. Operating on this assumption, an input displacement that exceeds the exposed distance without detecting a beginning and end of a stroke based on operator contact with the input device may be indicative of an unintentional displacement of the input device. Accordingly, some implementations include the preset travel distance as the distance threshold that represents to the control unit 610 that a received input at an input device was unintentional. The preset maximum travel distance, or distance threshold, may correspond to the exposed surface distance DS1 and DS2 or may be determined as a ratio of the exposed surface distance DS1 or DS2. In some implementations, the distance threshold may be a fraction of the exposed surface distance. In other implementations, the distance threshold may be a multiple of the exposed surface distance. Accordingly, the distance threshold may be greater than or less than the exposed surface distance. This may compensate for instances when an operator uses multiple fingers to advance, retract, or steer an elongate device using the input devices.

Several techniques are available for detecting an input displacement distance by an operator that is within an expected distance by an operator. For example, distance measurements on a displaced input device may be monitored via the motion sensors 682. Motion sensors may include, for example and without limitation, encoders, resolvers, optical sensors, hall effect sensors, and/or other mechanisms. The motion sensors may be disposed adjacent to input devices, on the input devices, or separated from the input devices. The motion sensors may monitor movement, such as rotation of the input devices. In an example, an optical sensor may be used to track the rotational surface distance traveled by an input device, such as the insertion/retraction control 440 and/or the steering control 460. As indicated herein, examples of the insertion/retraction control 440 and/or the steering control 460 include the scroll wheel and/or trackball. Accordingly, the control unit 610 may be configured to determine, based on the distance threshold, whether displacement is consistent with an expected displacement or inconsistent with the expected displacement. If the displacement is inconsistent with the expected displacement based on the distance threshold, the control unit 610 may operate to minimize a potentially adverse impact on a patient undergoing treatment.

Several techniques are available for detecting the presence of an operator at the input device(s). In some implementations, detecting the presence of the operator at the input device includes detecting affirmative contact with the insertion/retraction control and/or the steering control by the operator. In some examples, one or more operator-detection sensors 684 associated with the insertion/retraction control and/or the steering control may be used to detect actual operator contact with the insertion/retraction control and/or the steering control using affirmative contact sensors. Such affirmative contact sensors may include, for example, capacitive touch sensors associated with, for example, the scroll wheel and/or trackball, that are able to differentiate between touch by the fingers of the operator and contact with foreign objects, including the floor, instruments, devices, tools, and/or the like. In some examples, the one or more affirmative contact sensors forming the operator-detection sensors 684 may be pressure sensors, such as a contact switch, strain gauge, and/or the like between the scroll wheel and/or trackball and the molding in which the scroll wheel and/or trackball sits and/or between the molding and the body of the input control console. When sufficient downward pressure on the scroll wheel and/or trackball are detected, such as by the fingers of the operator, affirmative contact may be detected.

Other types of operator-detection sensors 684 may be used to detect the presence of an operator at the input device. For example, one or more proximity sensors may be used to detect the presence of fingers and/or hands above and/or near the input controls and/or to detect fingers, hands, wrists, and/or fore arms above or near the upper surface of the input control console. In some examples, the one or more proximity sensors may include one or more ultrasonic sensors, one or more vision sensors, one or more light walls, and/or the like. In some examples, data from the proximity sensors may be evaluated using one or more pattern and/or image processing techniques to differentiate the operator from other foreign objects in the vicinity of the input control console. In some examples, one or more pressure and/or touch sensors located in a wrist rest in front of each of the input controls may be used to detect the presence of a wrist and a corresponding hand near the one or more input controls. In some examples, the input control console may optionally include one or more accelerometers to determine whether recent sudden motion of the input control console has occurred, the input control console is not oriented in a sufficiently upright orientation (e.g., such as the orientations permitted by one or more paddle levers of input control console 400), and/or the like.

In some embodiments, one or more affirmative contact activities may be used to detect affirmative contact of the operator with the one or more input controls. In some examples, one or more pressure sensors associated with the input controls may be used to detect a wake-up activity, such as a double-press/double click of the corresponding input control, a press and hold for a minimum duration of the corresponding input control, and/or the like. In some examples, the wake-up activity may be used as a precursor action before allowing motion indicated by the corresponding input control to be passed on to the controlled device. In some examples, other wake-up like precursor activities may include one or more of a minimum affirmative contact period (e.g., 0.05 to 0.5 seconds or more and/or other period that does not place an unreasonable delay in the operator being able to begin control of the controlled device after the operator makes affirmative contact), a minimum affirmative contact period (e.g., 0.05 to 0.5 seconds or more and/or other period that does not place an unreasonable delay in the operator being able to begin control of the controlled device after the operator makes affirmative contact) without motion of the corresponding input control above a threshold, a wiggle or other specified pattern in the corresponding input control, engagement of a secondary control (e.g., a foot pedal), and/or the like before allowing use of the corresponding input control.

Figure 8:
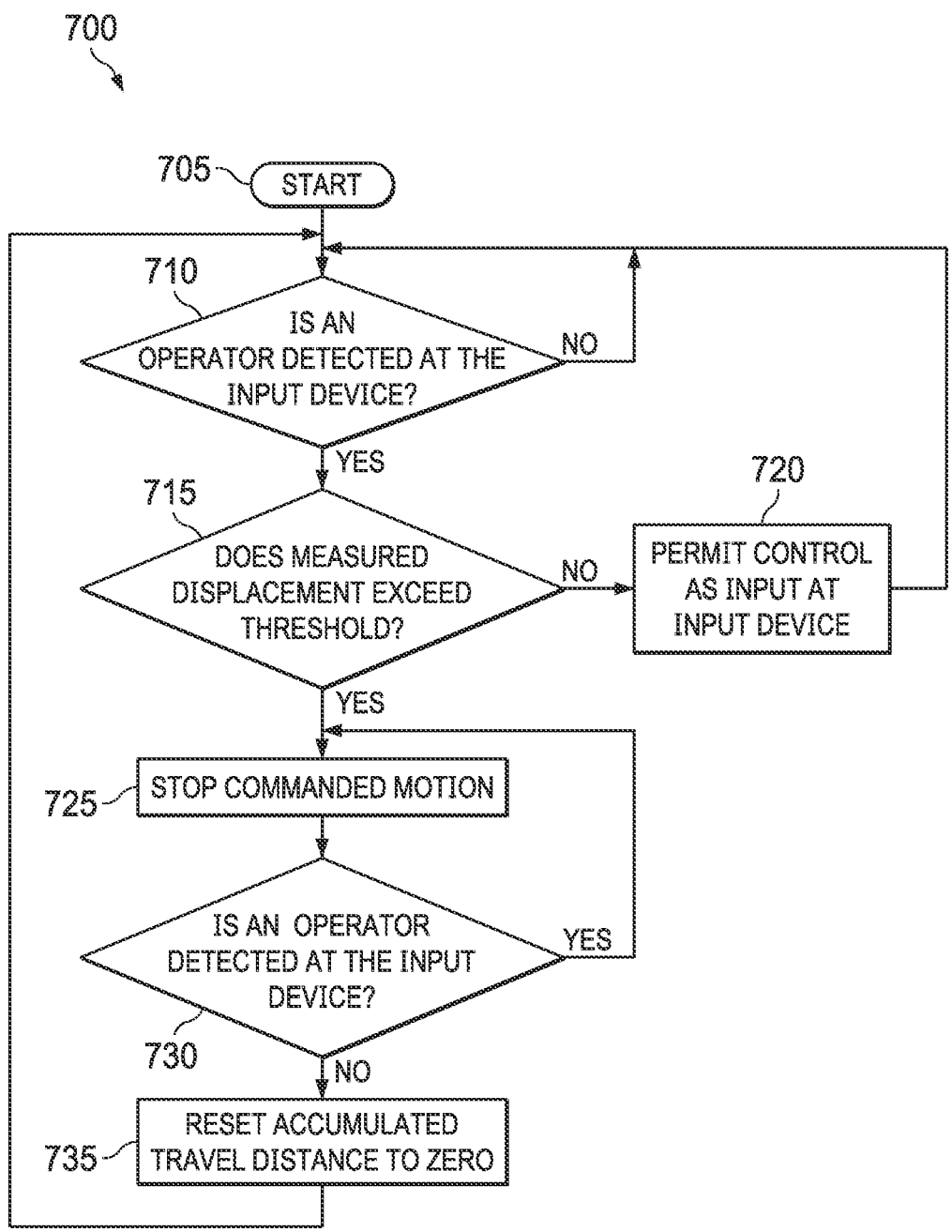
FIG. 8 is a simplified diagram of a method of operating a controlled device according to some embodiments.

FIG. 8 is a flowchart showing an example method 700 of operating a controlled device according to some embodiments. The method may include a plurality of processes or blocks to distinguish between intentional control inputs from an operator and unintentional control inputs that may occur from time to time. As indicated above, unintentional control inputs may occur when an input device is unintentionally bumped, displaced, dropped, or otherwise activated to generate an input signal without active intent by an operator. One or more of the blocks of method 700 may be implemented, at least in part, in the form of executable code stored on non-transitory, tangible, machine-readable media that, when run by one or more processors (e.g., the processor 620 in control unit 610), may cause the one or more processors to perform one or more of the blocks. For the purposes of illustration, method 700 is described in a context where the controlled device is a computer-assisted medical device, such as the elongate device of FIGS. 1-3B, using an input control console, such as input control console 400 having an insertion/retraction control and a steering control.

As described herein, the control system 600 may be configured to cooperatively rely upon dual sensor readings to determine whether an input at the input device is an intentional input from an operator. The control system 600 may rely upon the operator-detection sensors 684 to detect the presence of an operator and may additionally rely upon the motion sensor 682 to confirm that the actual input (movement) at the input device is within an expected and acceptable range.

The method 700 may begin at a start block 705. At 710, the process may determine whether an operator is detected as being present at the input device. Whether an operator is present may be determined based on the operator-detection sensor 684. As described above, in some implementations the operator-detection sensor 684 is a capacitive touch sensor associated with the input device. The capacitive touch sensor may be configured to identify when the input device is in physical contact with structure having capacitance in the range of human skin. Accordingly, an operator's hand on the input device may be detected by the capacitive touch sensor. As described herein, other types of sensors may be indicative of the presence of an operator and may be relied upon by the control unit 610 of the control system 602 to detect the presence of an operator. If at 710 an operator is not detected by the operator-detection sensor 684, the control system might not take action but may continue to monitor for a signal indicating an operator is present.

If at 710, operator-detection sensor 684 detects that an operator is present at the input device, then the control system 600 may proceed to block 715. At block 715, the control system may detect a displacement distance of the input device with the motion sensor 682, and may determine whether the detected displacement distance of the input device exceeds a distance threshold (e.g., a prestored distance threshold). In some implementations, the control system measures the accumulated travel distance of the input device with the motion sensor 682 during the entire period that an operator is detected at the input device. For example, the motion sensor 682 may detect a displacement distance of 1.5 times the exposed surface distance of the insertion/retraction control 440 while the operator is affirmatively in contact with the insertion/retraction control 440. As indicated above, the distance threshold may be stored in the memory 630 and compared by the control unit 610 to the actual measured displacement distance of the input controls 670. As indicated above, some implementations of the distance threshold may be substantially equal in distance to the stroke distance DS1 and/or DS2 of the input device. Since the insertion/retraction control 440 and the steering control 460 have different diameters or may be placed at different depths in the input control console, the distance threshold may be different for each. In some embodiments, the distance threshold is greater than or less than the stroke distance of the input device. In some implementations, the distance threshold is in the range of about two full stroke distances of the scroll wheel or trackball.

In some implementations, at 710, instead of determining whether the displacement distance exceeds the distance threshold, the control system 600 may be configured to measure whether a velocity exceeds a velocity threshold for a certain duration. In such a system, instead of using motion sensor 682, the control system may employ velocity sensors capable of detecting a velocity of rotation or velocity of an input at the input control 670 of the control system 600.

Also, or alternatively, the control system 600 may determine the velocity of rotation and/or velocity of an input by determining the displacement distance (e.g., detected by the motion sensor 682) over a period of time.

If at 715, the displacement distance does not exceed the distance threshold, then at 720, the control system 600 may permit the control system to generate a control signal to control the device 650 (which may correspond to the elongate device 202) as commanded by the input control 670 (which may correspond to the insertion/retraction control 440 and/or the steering control 460).

If at 715 the displacement distance does exceed the distance threshold, then the control system 600 may stop all commanded motion at 725. This may include preventing controls signal generation. Accordingly, if the sensed displacement travel distance exceeds the distance threshold, then the commanded motion may be an unintentional and undesired input at the input controls. By stopping a commanded motion at 725, the control system 600 may prevent undesired trauma to the tissue of a patient. As used herein, stopping a commanded motion may include preventing a control signal from being generated at the control application 640 and communicated to the controlled device 650. Accordingly, the control device (which may correspond to the elongate device 202) will not be further advanced into the patient. In some implementations, stopping or preventing a commanded motion might only prevent commands relating to insertion of the controlled device. In other implementations, stopping or preventing a commanded motion may prevent commands relating to insertion and retraction. In yet other implementations, stopping or preventing a commanded motion may prevent commands relating to insertion, retraction, and steering (e.g., pitch and yaw) movement are all prevented. Other arrangements are also contemplated.

An advantage of the dual sensing system described herein is that the command signal might not be generated without an operator having been detected at the input device at 710, and might not be generated if the displacement distance of the input device exceeds the distance threshold (e.g., a preestablished distance threshold). The dual system may reduce the chance of an unintentional command in the event of a false positive from the operator-detection sensor 684 at 710. This may be useful when certain types of material or fluid (such as saline) are accidentally spilled on the input control console. Such materials or fluids may be detected by a capacitance sensor forming a part of the operator-detection sensor 684 and may cause a false reading indicating that an operator is present when he or she is not. Even in the event of a false positive of the presence of an operator, if the travel distance at the input device exceeds the distance threshold at 715, the control system 600 may prevent further commanded motion at 725.

Continuing on, the control system may prevent generation of motion commands until a change in state, which may include an operator being not detected at the input device. Accordingly, the input may be required to make a change from the false positive. Accordingly, if commanded motion is stopped at 725, the method may seek to detect whether an operator is present at 730. If yes, then the system may continue to prevent commanded motion at 725. Detecting that an operator is present at 730 after an input exceeds a travel distance threshold at 715 may be indicative of a false positive. Accordingly, commanded motion may be prevented at 725 until an operator present signal is not detected at 730. In some implementations for example, the false positive of an operator being detected as present at 730 might not be able to be changed until a material or fluid, such as saline, is cleaned or removed from contact with the input device, thereby allowing the operator-detection sensor 684 to show an operator is not present, which thereby allows the system to reset.

Thus, if an operator is not detected as being present at 730, the tracked and accumulated travel distance may be reset to zero at 735, and the control system may be reset to provide control as commanded at an input device. The method may return to 710 where the system monitors the operator-detection sensor for the presence of an operator. As used herein, the tracked travel distance is the accumulated travel distance of the input device since the last time that an operator present signal was detected. Utilizing both operator-detection sensors 684 and motion sensors 682 may provide a more reliable system for detecting intentional operator inputs and preventing excessive unintentional displacement of a medical device.

Figure 9:
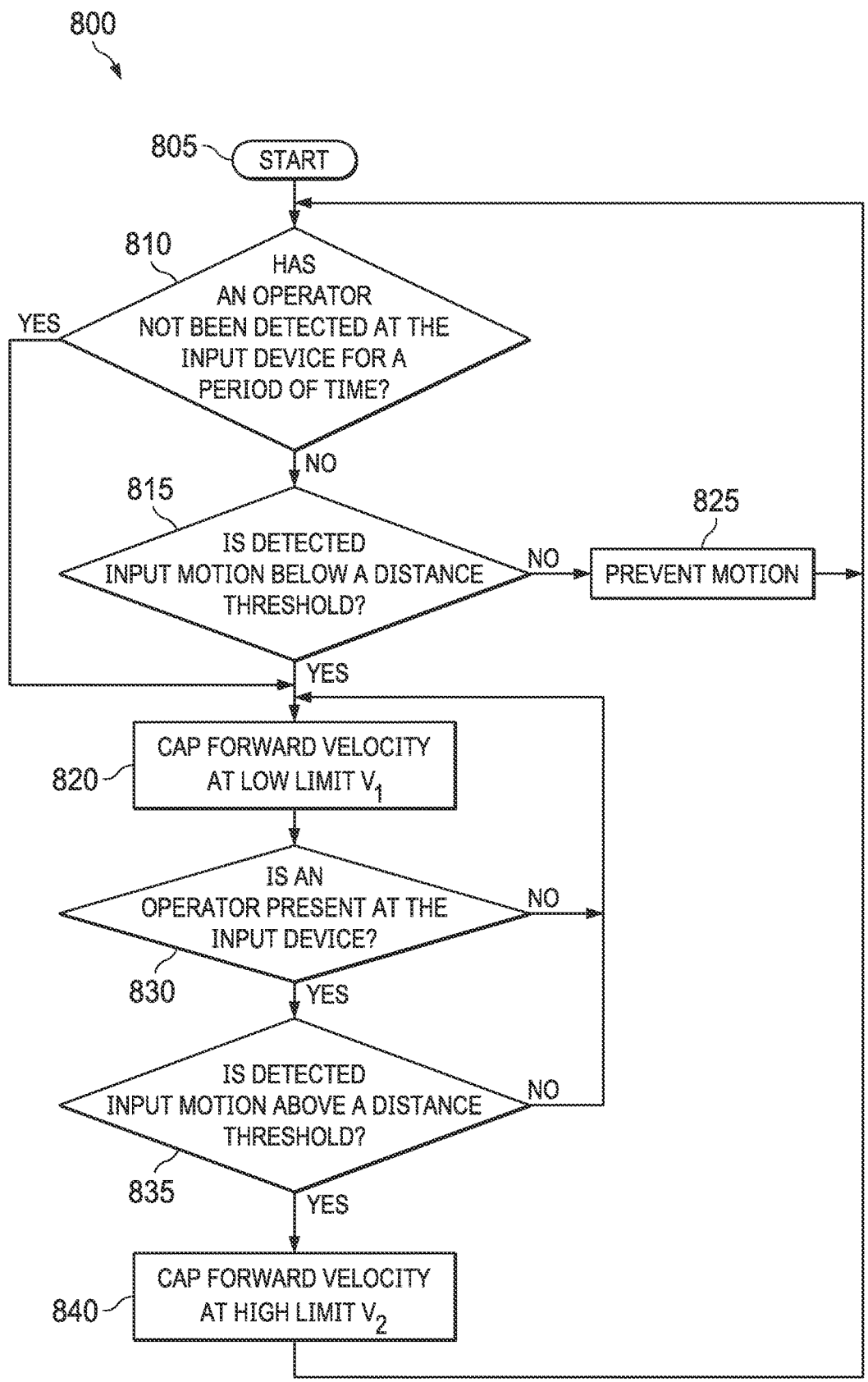
FIG. 9 is a simplified diagram of a method of operating a controlled device according to some embodiments.

FIG. 9 is a flowchart showing another example method 800 of operating a controlled device according to some embodiments Like the method 700, the method 800 executes a plurality of processes or blocks to distinguish between intentional control inputs from an operator and unintentional control inputs that may occur from time to time. Like the method 700, the method 800 may be run by one or more processors (e.g., the processor 620 in control unit 610) and may cause the one or more processors to perform one or more of the blocks.

The method 800 includes a velocity limit to address a situation where an operator accidentally makes contact with the input device. If an operator hits or brushes up against the input device with enough force or contact, operator-detection sensor 684, which may include a capacitive touch sensor, may detect the presence of an operator, and the motion sensor 682 may detect a high velocity movement. Without appropriate safeguards, the control system may generate an undesired control signal, potentially harming the patient. The method 800 provides a velocity limit that may be capped at a low value when the presence of an operator is not detected. Thus, when the presence of an operator is detected with confidence, the velocity limit may be increased to a higher velocity limit. With continued detection of the presence of an operator, the velocity may remain at the higher velocity limit or cap. However, when the operator-detection sensor 684 no longer detects the presence of an operator, the velocity limit or cap may be reset to the initial low velocity cap. Thus, if the input device was accidentally touched, the resulting commanded motion might be applied at a very low velocity, resulting in minimal risk to patient anatomy. However, if the input was intentional, and the operator was actively actuating the input device, the control system may generate a command initially at a low velocity, but may ramp to a working velocity which in some implementations may appear relatively seamless to the operator.

The method in FIG. 9 will be described with reference to the graph in FIG. 10, which shows an example velocity profile having a lower velocity cap V1 and a higher velocity cap V2.

The method begins at 805. At 810 and 815, the system may determine whether the input device is in a no contact state. To do this, at 810, the control system 600 may determine whether an operator has not been detected at the input device for a period of time. In some implementations, the period of time may be a preestablished time period, which may be prestored in the control application 640 of the control system 600. The absence of an operator at the input device may provide time for the system to reset and start fresh when signals are detected. In some implementations, the time period or threshold may be, for example, within a range of about 0.1 seconds to about 5 seconds. In some implementations, the time period range may be about 0.25-1.0 seconds. The ranges here are the example ranges, and both larger and smaller limits and ranges are contemplated.

If at 810, an operator has not been present (or has been absent) for a period of time longer than the time period, then at 820 the control system may cap forward velocity at a low limit V1. If at 810, an operator has been present (has not been absent) for a period of time longer than the time period, then at 815 the control system may detect and compare an input motion (e.g., displacement distance) of the input device to a distance threshold (e.g., a preset distance threshold). If at 815 the control system determines that the detected motion is not below a distance threshold (e.g., is above the distance threshold), then the system may prevent motion at 825. This scenario may arise when an operator appears to be present based on the operator-detection sensor, but the measured input device motion is greater than would be expected. A motion distance greater than expected may be evidence that the detected input device motion was inadvertent.

At 825, motion may be prevented by preventing the control unit 610 from generating a motion command to advance, retract, or steer the controlled device 650. The system may continue to prevent motion until it detects at 810 that an operator present signal has been absent for the preset period of time.

If at 815, the detected input motion is below the distance threshold, then the command may be executed, and the forward velocity may be capped at the low velocity limit V1.

Figure 10:
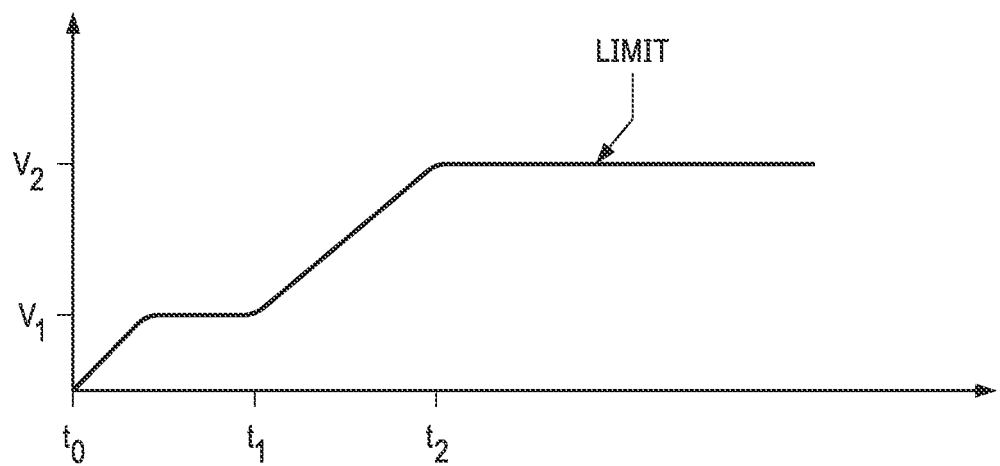
FIG. 10 is a graph showing a velocity cap profile utilized to control a device according to some embodiments.

FIG. 10 shows the velocity profile with the velocity cap shown as V1 for the time period between t0 and t1. As can be seen, in some implementations, the cap may ramp to the low velocity limit V1 as shown, while in other implementations, the cap is stepped. Operation may continue with the forward velocity capped at V1 until a change in state.

Continuing in FIG. 9, the processes 830 and 835 may indicate to the control system 600 whether the system is to operate in a voluntary contact state where the capped velocity may be increased from the low velocity limit V1 to a higher velocity limit V2, as shown in FIG. 10.

At 830, the control system may determine whether an operator is present at the input device. This may include detecting whether the input device has been touched often enough to rule out noise from the operator-detection sensors 684.

If the operator is not detected as being present at 830, then the velocity may continue to be capped at the low limit V1. If the operator is detected as being present at the input device at 830, then the system may, at 835, determine whether the detected input motion (e.g., the measured displacement distance) is above a distance threshold. If the detected input motion is not above a distance threshold at 835, then a potential scenario is that a small input at the input device was not intended, and the forward velocity may remain capped at the low velocity limit V1.

If at 835 the detected input motion is above the distance threshold, then a potential scenario is that a larger input at the input device was intended, and at 840 the forward velocity may be increased to the higher limit V2. FIG. 10 shows the velocity cap increasing from t1 to t2 and then being maintained at V2. In some implementations, the transition from the lower velocity limit V1 to the higher velocity limit V2 occurs progressively. In such a system, the longer that the system is positive at 830 and 835, the higher the forward velocity limit up to the high velocity limit V2. In other implementations, the transition from the lower velocity limit V1 to the higher velocity limit V2 occurs in a single step. Returning to FIG. 9, the forward velocity may be capped at the high velocity limit V2 at 840 until the operator present signal is absent for a period of time longer than the time threshold at 810.

In some implementations, the systems and methods described herein are applied to insertion commands from the insertion/retraction control 440, but limits might not be applied to a retraction commands. In other implementations, the systems and methods may be applied to both insertion and retraction commands.

In some implementations, the control system may limit the amount of motion of the medical device inside the patient that may occur as a result of a temporary, involuntary contact with the input device. Accordingly, the control system may include or have stored in memory a motion threshold that may be a distance that is clinically acceptable for motion inside of the patient. Commanded motion that exceeds the clinically acceptable motion threshold when the medical device is disposed within a patient may be prevented. In some implementations, the clinically acceptable motion threshold may be about 6 mm or less, such as between about 0 and 6 mm. That is, an input at the input device may be carried out so long as it is below a motion threshold even before the control system determines whether the input was intentional or unintentional. If the input at the input device were to initiate a command that exceeds the motion threshold, then the motion might be prevented. In other implementations, the clinically acceptable motion threshold may be about 4 mm or less, such as between about 0 and 4 mm, and in yet others, 2 mm or less, such as between about 0 mm and 2 mm. In yet other implementations, the clinically acceptable motion threshold may be about 1 mm or less such as between about 0 and 1 mm. Since an input motion is carried out if the command is below the clinically acceptable motion threshold, the inverse may also be true such that the command may not be carried out if it exceeds or is above the clinically acceptable motion threshold. For example, if the input at the input device were to initiate a command that exceeds a motion threshold of 4 mm, then the motion might be prevented.

In some implementations, the motion threshold may be a condition for selecting the velocity limit described above. Accordingly, the motion threshold may be dependent on not only whether the medical device is disposed within a patient, but where the medical device is disposed within the patient. For example, if the medical device is near highly sensitive tissue or organs, the motion threshold may be smaller than if the medical device is near lower sensitivity tissue or organs. In addition, the motion threshold may be dependent on the medical procedure being performed. For example, the motion threshold may be larger if the medical procedure is one that would expect a larger range of motion of the medical device, while the motion threshold may be smaller if the medical procedure is one that would expect a smaller range of motion of the medical device. In some implementations, multiple factors, such as the location of the medical device in the patient and the type of procedure being performed, are used together to determine the motion threshold. Accordingly, the motion threshold may be dynamic and change over time throughout the medical procedure. In some implementations, the motion threshold is correlated with the velocity threshold described herein.

In some implementations, the control system is configured to preserve system responsiveness to small voluntary motions that occurred during the detection time that the algorithm needs to determine whether a was voluntary or involuntary. This may help the control system provide fine and sensitive control of the medical device and provide a good teleoperational experience to the operator. That is, even while the control system is determining the presence of an operator or determining whether an input was intentional or unintentional, the control system may continue to generate control signals to move the medical device. As indicated above, these control signals may be tempered or limited by the motion threshold. This fine and sensitive control may be helpful when the medical device is a catheter tip control to carry out a biopsy, for example. That is, the control unit may be configured to generate the control signals during the time period that the control unit is detecting whether the operator is present so long as the input at the input device is requesting displacement of the medical device a distance below a displacement threshold.

As described herein, in some implementations, presence of the operator is detected utilizing the detected capacitance level of the input controls 670 in FIG. 7, such as the insertion/retraction control 440 and/or the steering control 460. For example, the input controls 670 may detect the presence of the operator by detecting or measuring the capacitance level of the insertion/retraction control 440 and/or the steering control 460. However, the capacitance level may also vary due to environmental conditions, such as, for example, temperature changes within the room in which the input controls 670 reside and moisture levels, including humidity or the presence of liquids on the input controls 670. Accordingly, in order to reduce the likelihood of misreading a command at the input controls 670, some implementations include a calibration process. Calibration may be performed when the medical system 100 is powered-up, such as at an initialization procedure. Calibration also may be performed when the medical system 100 has been in use and an unexpected event occurs. Accordingly, in some implementations, calibration may occur when an input is received that was unexpected based on the task being performed.

In some implementations, calibration of the medical system 100 identifies and sets capacitance operating levels that may be utilized to identify and distinguish a desired input command from an inadvertent or unintentional command. These capacitance operating levels are referred to herein as a baseline level and a command line level. The baseline level may be the capacitance level when an operator is not touching the input controls 670. The command line level may be the capacitance level where the system will generate a positive command to move the elongate device in response to an input at the input controls 670. The command line level may also be referenced herein as a command capacitance level.

Figure 11:
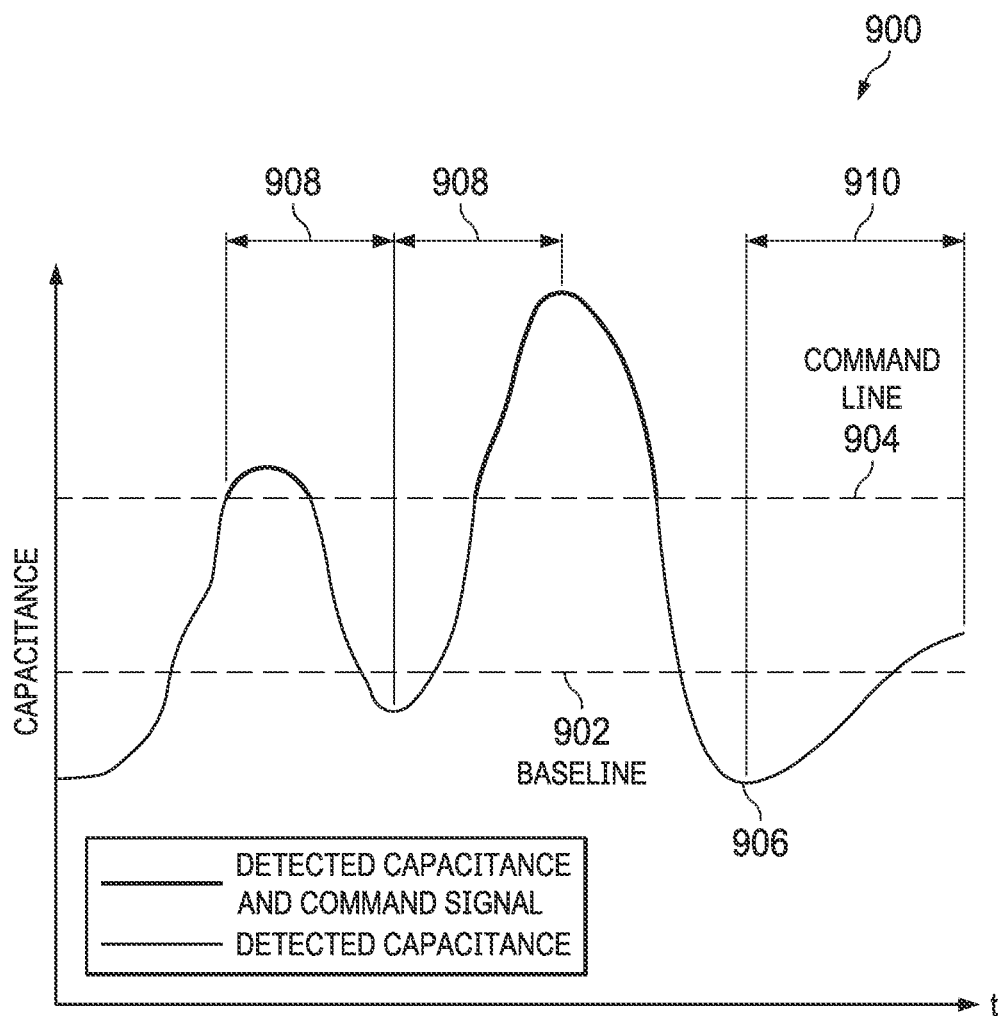
FIG. 11 is a graph showing capacitance over time according to some embodiments.

FIG. 11 is an example graph 900 showing an example baseline level 902, an example command level 904, and a detected capacitance level 906 that may be detected via the operator detection sensors 684 (FIG. 7). The calibration procedure may be used to establish the baseline level 902 and the command level 904. The detected capacitance may be detected or measured at the input controls 670 and may represent contact by an operator with the input controls 670.

Referring to FIG. 11, the baseline level 902 may be established as a capacitance level when the operator is not touching the input controls 670. This baseline level 902 may be established as a moving average of a raw capacitance sensor reading over a period of time, such as a window of time. The sensor detecting the raw capacitance may be an operator detection sensor 684 described with reference to FIG. 7. In some implementations, the baseline level 902 is established to match a moving average of the raw capacitance over a window size between about 1 and about 5 seconds. In some implementations, the window of time period is about three seconds. Other window of time periods are contemplated.

Once the baseline level 902 is established, the command line level 904 may be established based on a designated capacitance offset from the baseline level 902. For example, if the baseline level is established to be at three units of capacitance, and if the command line level were offset from the baseline level by two units, then the command line level would be five units. The fixed offset may be based on a fixed value, such as two units above the baseline, or may be a fixed level based on a fixed calculation taking into account the baseline level value. For example, an offset calculation that takes into account the baseline level may be the baseline level value plus 50% of the baseline level value. Other equations for establishing the offset are contemplated.

With the baseline level and command line levels established in FIG. 11, the control unit 610 may be operable to issue command signals when the detected capacitance exceeds or is greater than the command line level 904. In FIG. 11, the curved line represents detected capacitance level 906 over time in one scenario. The detected capacitance level 906 is represented by a narrow line portion when below the command line level 904 and a thick or bolded line portion when above the command line level 904. When the detected capacitance level 906 is below the command line level 904, the control unit 610 might not issue a command to displace the controlled device 650, even when the detected capacitance level is above the baseline level 902. In contrast, when the detected capacitance level 906 is above the command line level 904, the control unit 610 may issue a command to displace the controlled device 650 when such a command is requested at the input controls 670.

Environmental factors may impact the average capacitance reading over time, causing the average capacitance reading to change. For example, this may be due to temperature changes, humidity changes, or other environmental changes. In these instances, the average capacitance reading while an operator is not touching the input control 670 may begin to deviate from the baseline 902. Furthermore, if the operator is touching the input control 670 during a baseline calibration, the baseline level 902 may be established too high, resulting in a command line level 904 that is too high. This may cause the control system 600 to not detect user contact, which could cause the medical system 100 to be unresponsive.

When these events occur, a calibration process may be used to reset or shift the baseline level and the command line level. This example process may also be utilized during initialization or startup to establish the baseline level and the command line level.

In some implementations, the calibration process may form a portion of the control application 640 in the memory 630, shown in FIG. 7. The control application 640 may include one or more calibration modules for establishing or resetting the baseline level 902 and the command line level 904 that are used to determine whether the control system 600 can issue control signals to control the controlled device 650. Accordingly, the control application 640 may include one or more thresholds, processes or methods relied upon to calibrate the medical system 100. In addition, the calibration levels may be detected using the operator-detection sensors 684 described herein. In some implementations, the operator detection sensors 684 detect actual operator contact with the insertion/retraction control and/or the steering control using affirmative contact sensors that may include, for example, capacitive touch sensors. However, as described herein, the operator detection sensor 684 may also be pressure sensors or other sensors.

Figure 12:
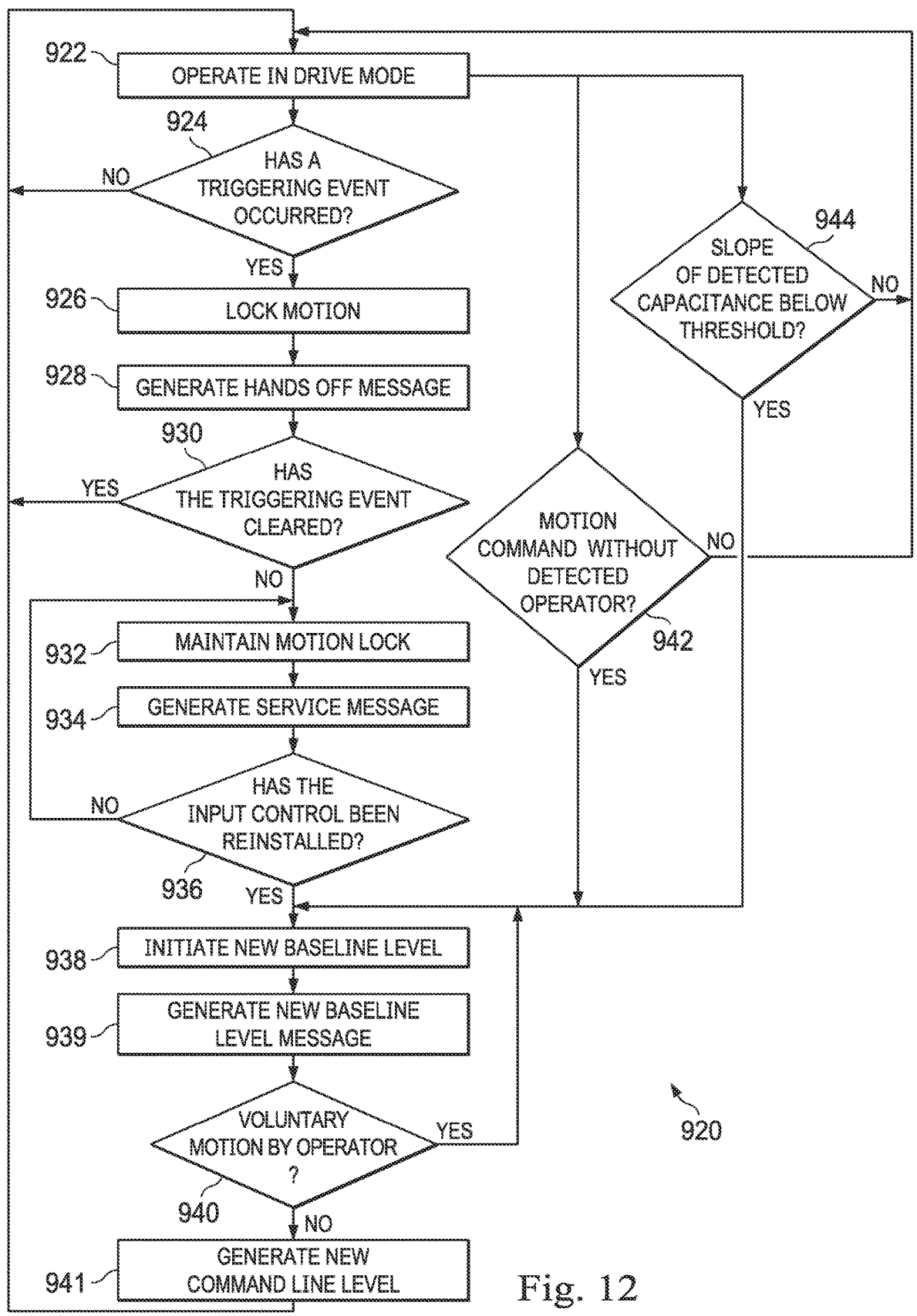
FIG. 12 is a simplified diagram of a method of operating a controlled device according to some embodiments.

FIG. 12 is a flowchart showing an example method 920 of calibrating or recalibrating the control system 600 according to some embodiments. The method 920 executes a plurality of processes or blocks to set up, and then adjust the baseline level. Like other methods described herein, the method 920 may be run by one or more processors (e.g., the processor 620 in control unit 610) and may cause the one or more processors to perform one or more of the blocks. For purposes of illustration, the method 920 is described in a context where the controlled device is a computer-assisted medical device, such as the elongate device of FIGS. 1-3B, using an input control console, such as the input control console 400 having an insertion/retraction control and steering control.

At 922, the medical system 100 may be in a drive mode. The drive mode may represent a mode where the medical system 100 is operable and responsive to inputs from an operator. The method may also start with the medical system in an initialization mode, representing the beginning of a startup process or an initialization process that may occur when the medical system 100 is switched on or powered up from an unpowered state.

At 924, the system may query or check whether a triggering event has occurred indicative that the capacitive detection of the input device may be stuck or otherwise inoperable. Some examples of potential triggering events are described herein with reference to FIG. 8, where the control unit 610 determines whether the displacement distance of input control 670 exceeds an unacceptable displacement distance or whether a velocity exceeds a velocity threshold for certain duration of time. Other triggering events are contemplated.

Returning to FIG. 12, if at 924, a triggering event is not detected, then medical system 100 may continue to operate in the drive mode (e.g., in 922). In the drive mode, operator commands issued via the input control 670 may be translated, by the control unit 610, to corresponding movements of the elongate device 202 (e.g., insertion, retraction, and/or steering movements). However, if such events, such as those described with reference to FIG. 8 are discovered at 924 then, at 926, a motion lock may be activated. A motion lock may stop the control system 600 from issuing signals for commanded motions. This motion lock may correspond to the stop commanded motion block at 725 in FIG. 8.

After activating the motion lock at 926, the control system 600 may generate a hands-off message for an operator to remove hands from one or more of the input controls 670 prior to again permitting regular control of the elongate device. This message may include specific instructions to remove hands or otherwise to not contact the insertion/retraction input control and/or the steering input control. In some implementations, the message to an operator to remove hands from the input controls may be a visual message, such as flashing indicator lights or text displayed on a display readable to the operator. In other implementations, the message to an operator may be an audible instruction to the operator, achieved through speakers. In yet other implementations, the message may be both visual and audible.

At 930, the control system 600 may determine whether the triggering event cleared when the operator removed hands at 928. In some implementations, the control system 600 may do this by detecting a change in the sensed or detected capacitive level in response to the hands-off message at 928. For example, if the detected capacitive level 906 in FIG. 11 immediately drops below the command line 904, then the control system 600 may reactivate regular control in the drive mode at 922 as shown in FIG. 12. However, if at 930 the triggering event is not cleared, then the control system 600 may maintain the motion lock at 932 and may generate a service message at 934.

At 934, the control system 600 may generate a service message to the operator. In some implementations, the service message may include a prompt to remove the input controls 670, clean the controls or the control console, and return the input controls 670 to their operable positions. As with the hands-off message 928, the service message 934 may be a visual message or an audible message, or both. Cleaning the input controls 670 and/or the console may address some situations that lead to an undesired detected capacitance level. For example, liquid disposed on the console may undesirably alter the sensed capacitive readings of the input controls 670.

At 936, the control system may determine whether the input controls have been reinstalled. The control system may do this using proximity sensors, pressure sensors, or other sensors that may be utilized to indicate the state of assembly of the console. In other implementations, the control system 600 may await an input from the operator indicating that the control device has been installed. If at 936, the control device(s) are not installed, then the control system 600 may maintain the motion lock at 932 and may continue to display the service message at 934. Once the control device is installed at 936, the calibration process may reinitiate at 938.

At 938, the control system 600 may initiate a new baseline level. For example, the control system 600 may establish the baseline level by determining a moving average of raw capacitance sensor readings over a period of time. As described above, in some implementations, the period of time may be between about 1 second long and about 5 seconds long. In some implementations, the period of time may be about 3 seconds long. During this baseline initiation process, the control system 600 may communicate a message to the user that a baseline is being established at 939. In some implementations, the message to the user that a baseline is being established may include instructions for the operator, such as for the user not to touch one or more of the input control(s). As with the other messages described in the method 920, the message for the baseline at 939 may be in any form of communication including visual and/or audible.

At 940, the control system 600 may monitor the one or more input controls for voluntary motion by the operator. If at 940, the control system 600 detects a voluntary motion at the input control by the operator, then the control system may return to 938 and restart the initialization process for the new baseline level. That is, if the operator inputs a voluntary motion at the input device, then the baseline level initiation process restarts so that the baseline level may be established without interference of the operator. If at 940 the control system 600 does not detect voluntary motion by an operator, then the control system may continue to establish the new baseline level.

After the period of time at 938 and 939 without voluntary motion from the operator, the baseline level 902 may be established. Once the baseline level 902 is established, the command line level 904 may be generated or established at 941. In some implementations, the command line level may be established as a calculated offset based on the baseline level. With the baseline level and the command line level established, the drive mode may be reactivated at 922.

The baseline level and/or command line level may be established for one input control (e.g., the insertion/retraction control 440 or the steering control 460) or for multiple input controls (e.g., both the insertion/retraction control 440 and the steering control 460). The baseline level message generated in 939 may indicate to the operator which input control(s) are being recalibrated. For example, if only the baseline level for the insertion/retraction control 440 is to be recalibrated, the baseline level message generated in 939 may request the operator not to touch the insertion/retraction control 440 during calibration. If only the baseline level for the steering control 460 is being recalibrated, the baseline level message generated in 939 may request the operator not to touch the steering control 460. If baseline levels for both the insertion/retraction control 440 and the steering control 460 are being recalibrated, the baseline level message generated in 939 may request the operator not to touch the input control console 400.

The example method in FIG. 12 also includes another path for initiating a new baseline level. While operating in the drive mode at 922, the control system 600, at 942, may monitor (e.g., continuously monitor) for motion commands detected without detecting presence of an operator (e.g., voluntary motion commands while the sensed capacitance is at or is below the command line). In other words, a voluntary motion request might be detected even though the control system does not detect the presence of an operator. This scenario may be indicative of a baseline level established at a level incompatible with an operator input. For example, if the baseline level was previously established while the operator was in contact with the input control(s) 670, the baseline level might be too high. Then, when the operator requests movement by touching and moving the input control(s) 670, the detected capacitance might be below the command line level. Thus, the control system 600 might be unresponsive to actual commands input by the operator.

If a voluntary motion is detected without detecting the presence of an operator at 942, the method 920 may proceed to 938 and attempt to establish a new baseline. The method may continue as described above, with generation of a new baseline level message at 939, monitoring for voluntary motion by an operator at 940, and a command line level being established at 941 and then the drive mode being reactivated at 922.

In some implementations, the control system 600 may monitor for motion commands detected without a detected operator (e.g., in operation 942) by monitoring the duration of the motion request. In some examples, this may include monitoring the travel distance of an input control 670, such as the insertion/retraction control 440 (e.g., a scroll wheel) or the steering control 460 (e.g., a trackball). As an example, if the travel distance of the input control is high, as may occur via a fast spin of a trackball or scroll wheel with the detected capacitance below the command line level 904, then the control system 600 may recognize this as an unexpected or inadvertent input rather than a voluntary motion command. Because the input (e.g., a fast spin) is inconsistent with an expected control input, the control system 600 may recognize this as an inadvertent input. In contrast, if the travel distance of the input control 670 is a slow, longer duration voluntary motion, then the control system 600 may determine that the input is consistent with an expected input or voluntary motion command at 942, and the control system may progress to establish a new baseline at 938.

In some examples, the difference between a voluntary motion (e.g., a control input expected for an operator) and input device motion not detected to be a command motion performed by an operator (e.g., a control input not expected for an operator) at 942 may be based on a duration of the motion and/or the distance that the input control moves over time (e.g., velocity). For example, if the velocity of the motion is greater than a threshold velocity, then the control system 600 may determine that the motion is inconsistent with a typical or voluntary motion from an operator, and therefore is inadvertent. In contrast, if the operator moves the input control a distance more slowly (e.g., the velocity motion is below a threshold velocity), the control system 600 may determine that the motion is voluntary motion (e.g., an expected control input), and the method may progress from 942 to 938 in FIG. 12. In some implementations, the control unit 610 may detect voluntary motion by an operator based on the duration of the motion. For example, the control unit 610 may determine that a motion is voluntary (e.g., operation 942: yes) when the duration of the motion is below a threshold duration and proceed to operation 938. As another example, the control unit 610 may be configured to determine that a motion is voluntary (e.g., operation 942: yes) and initiate the recalibration (e.g., in operation 938) based on the detected motion extending for a length of time between about 0.5 seconds and 5 seconds, and in some implementations, between about 0.5 seconds and 3 seconds.

The example method in FIG. 12 also includes yet another path for initiating a new baseline level. For example, while operating in the drive mode at 922, the control system 600 may monitor (e.g., continuously monitor) changes in the angle or slope of detected changes in capacitance at 944. For example, referring to FIG. 11, an abrupt or immediate change in detected capacitance level (e.g., represented by 908) may be indicative of user contact. Alternatively, a gradual change in detected capacitance level (e.g., represented by 910) may be indicative of creep that results from environmental conditions. Such creep may, over time, change the offset distance between the actual detected capacitance 906 and the command line level 904 even when an operator is not touching the input controls. This creep therefore could render the control system 600 either overly responsive or overly nonresponsive when an operator touches the input controls to control the controlled device 650.

Accordingly, in some implementations the control system 600 may monitor the slope of the detected capacitance over time to determine when the detected capacitance changes due to environmental conditions. For example, if the slope is below a particular threshold (e.g., a shallow slope), such as a change in one unit over 20 seconds, when an operator is not present, then the control system 600 may determine that creep has occurred, and that a new baseline should be established. When this occurs, the method 920 may begin to establish a new baseline at 938. The method may continue as described above, with a command line level being established after the baseline level and then the drive mode being reactivated at 922. If at 944 the change in slope of the detected capacitance is above a threshold (e.g., steep slope), then the control system may recognize this as a change due to an operator's touch. Accordingly, the control system may operate in drive mode at 922.

Figure 13:
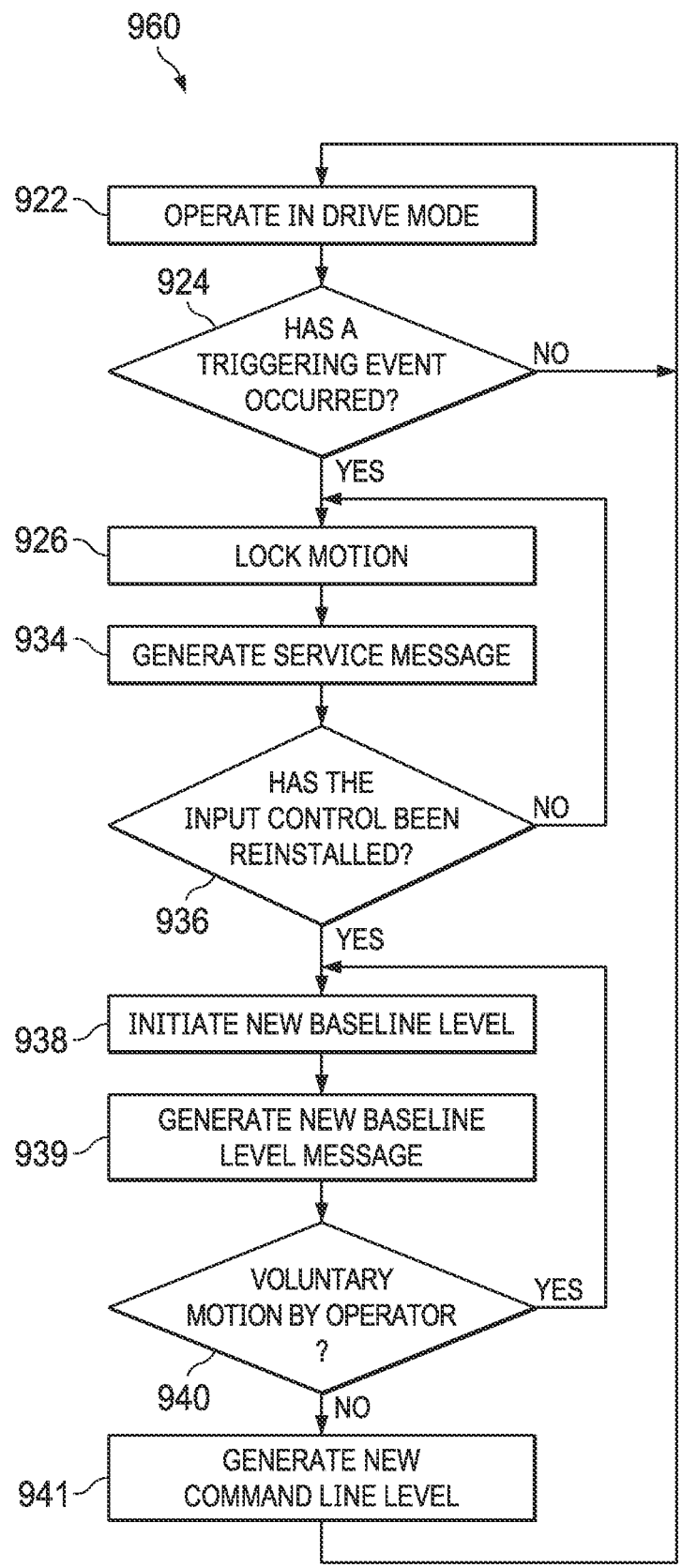
FIG. 13 is a simplified diagram of a method of operating a controlled device according to some embodiments.

FIG. 13 shows a simplified example method 960 of calibrating according to some embodiments. FIG. 13 includes many steps similar to those described with reference to FIG. 12 but is modified to allow a user to service the input controls and/or input console each time a triggering event is detected. The method of FIG. 13 includes operating the control system 600 in a drive mode at 922 as described above. The control system 600 may monitor for a triggering event as described above with reference to 924, and when a triggering event is detected, motion may be locked as at 926. In the method 960, when the motion is locked, the method may present the service message to the operator, at 934. Accordingly, the operator may be requested to remove and clean the input controls each time a triggering event occurs. Once the input controls are reinstalled at 936, the process continues to step 938 as described above. At 938, the baseline level is established. As the baseline level is established at 938, a baseline message may or might not be communicated to the operator, depending on the implementation. At 940, the control system 600 may monitor for voluntary motions by the operator. If voluntary motions are present at 940, the control system may return to 938 to restart the baseline level initiation. If voluntary motions are not present at 940, then the method may generate the new command line level at 941, as described with reference to FIG. 12.

In some implementations, during the period of time that the baseline is being established, the control system 600 may be temporarily unresponsive to motion requests. Once the baseline level and the command line level are established, the control system 600 may again be changed to the drive mode and control of the medical instrument may continue.

One or more elements in embodiments of this disclosure may be implemented in software to execute on a processor of a computer system, such as a control processing system. When implemented in software, the elements of the embodiments of this disclosure may be code segments to perform the various tasks. The program or code segments can be stored in a non-transitory machine-readable storage media, including any media that can store information including an optical medium, semiconductor medium, and/or magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented might not inherently be related to any particular computer or other apparatus. In addition, it will be appreciated that a variety of programming languages may be used to implement the examples described herein.

While certain examples have been described and shown in the accompanying drawings, it is to be understood that such examples are merely illustrative of and are not restrictive, and that the described examples are not be limited to the specific constructions and arrangements shown and described, since various other modifications may occur to those of ordinary skill in the art.

What is claimed is:

1. A system comprising:
    an input device structurally configured to be utilized by an operator to control a medical device;
    an operator-detection sensor associated with the input device and configured to detect a presence of an operator at the input device;
    a motion sensor associated with the input device and configured to detect a displacement distance of the input device; and
    a control unit configured to:
        permit or prevent control signal generation based on whether the detected displacement distance exceeds a displacement threshold for the input device while detecting that an operator is present at the input device,
    wherein the control unit is configured to reset an accumulated travel distance of the input device when an operator present signal is not detected.

2. The system of claim 1, wherein the operator-detection sensor comprises a capacitive sensor configured to detect when the operator is in physical contact with the input device.

3. The system of claim 1, wherein the control unit comprises the displacement threshold for the input device stored therein.

4. The system of claim 1, wherein the control unit is configured to prevent control signal generation when the detected displacement distance exceeds the displacement threshold while the operator-detection sensor detects that the operator is present at the input device.

5. The system of claim 1, wherein the control unit comprises a velocity cap stored therein, and wherein the control unit is configured to compare a motion detected by the motion sensor to the displacement threshold and limit movement of the medical device to a velocity at or below the velocity cap.

6. The system of claim 1, wherein the input device comprises one or more of a rollable scroll wheel or a rollable trackball.

7. The system of claim 1, wherein the motion sensor comprises an encoder configured to detect the displacement distance of the input device.

8. The system of claim 1, wherein the control unit stores a plurality of displacement thresholds including the displacement threshold, and wherein the control unit is configured to select the displacement threshold of the plurality of displacement thresholds based on a context of a medical procedure to be performed.

9. The system of claim 8, wherein the context of the medical procedure to be performed takes into account at least one of: a type of surgery to be performed, a surgical site to be treated, a presence of a vision probe, a location of the medical device relative to sensitive tissue in a patient body, or a detected force resistance against the medical device.

10. The system of claim 1, wherein the control unit comprises a displacement limit stored therein, and wherein the displacement limit prevents generation of control signals that would move the medical device a displacement distance greater than the displacement limit when the medical device is disposed within a patient.

11. The system of claim 10, wherein the displacement limit prevents generation of control signals when a request for displacement of the medical device greater than 4 mm is input at the input device and when the medical device is disposed within a patient.

12. The system of claim 10, wherein the displacement limit prevents generation of control signals when a request for displacement of the medical device greater than 2 mm is input at the input device and when the medical device is disposed within a patient.

13. The system of claim 1, wherein the control unit is configured to permit generation of control signals to displace the medical device in response to an input at the input device during a time period that the operator-detection sensor detects that the operator is present at the input device.

14. The system of claim 13, wherein the control unit is configured to permit generation of the control signals after determining that the input at the input device is a command to displace the medical device, the command being for a displacement less than the displacement threshold.

15. The system of claim 1, wherein the operator-detection sensor comprises a capacitive sensor configured to detect presence of an operator based on a capacitance level exceeding a command capacitance level, and wherein the control unit is configured to:
  during calibration of the command capacitance level, detect, via the motion sensor, voluntary motion of the input device by the operator; and
  based on detection of the voluntary motion of the input device, initiate a recalibration of the command capacitance level.

16. The system of claim 15, further comprising a display device, wherein the control unit is configured to:
  based on the detection of the voluntary motion of the input device, instruct the display device to display a message to the operator to not touch the input device.

17. A system comprising:
an input device structurally configured to be utilized by an operator to control a medical device;
an operator-detection sensor associated with the input device and configured to detect a presence of an operator at the input device;
a motion sensor associated with the input device and configured to detect a displacement distance of the input device; and
a control unit configured to:
  permit or prevent control signal generation based on whether the detected displacement distance exceeds a displacement threshold for the input device while detecting that an operator is present at the input device,
wherein the displacement threshold is less than or equal to an exposed surface distance of the input device.

18. A system comprising:
an input device structurally configured to be utilized by an operator to control a medical device;
an operator-detection sensor associated with the input device and configured to detect a presence of an operator at the input device;
a motion sensor associated with the input device and configured to detect a displacement distance of the input device;
a control unit configured to:
  permit or prevent control signal generation based on whether the detected displacement distance exceeds a displacement threshold for the input device while detecting that an operator is present at the input device; and
an output device structurally arranged to convey information to the operator,
wherein the operator-detection sensor comprises a capacitive sensor configured to detect presence of an operator based on a capacitance level exceeding a command capacitance level, and wherein the control unit is further configured to:
instruct the output device to output a message to the operator to not touch the input device during calibration of the command capacitance level.

19. The system of claim 18, wherein the output device comprises a display device, wherein the message comprises a visual message, and wherein the control unit is configured to instruct the display device to display the visual message during calibration of the command capacitance level.

* * * * *